(12) United States Patent
Hajduk et al.

(10) Patent No.: US 6,818,183 B2
(45) Date of Patent: Nov. 16, 2004

(54) MULTI-TEMPERATURE MODULAR REACTOR AND METHOD OF USING SAME

(75) Inventors: Damian A. Hajduk, San Jose, CA (US); Ralph B. Nielsen, San Jose, CA (US); Adam Safir, Berkeley, CA (US); Leonid Matsiev, San Jose, CA (US); Eric McFarland, Santa Barbara, CA (US); Paul Mansky, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/134,556

(22) Filed: Apr. 29, 2002

(65) Prior Publication Data

US 2002/0155036 A1 Oct. 24, 2002

Related U.S. Application Data

(63) Continuation of application No. 09/417,125, filed on Nov. 19, 1998, now Pat. No. 6,528,026, which is a continuation-in-part of application No. 09/177,170, filed on Oct. 22, 1998, now Pat. No. 6,548,026.
(60) Provisional application No. 60/096,603, filed on Aug. 13, 1998.

(51) Int. Cl.[7] .................. G01N 33/48; G01N 25/20; G01N 31/00; B01J 10/00; B32B 27/04
(52) U.S. Cl. .................. 422/68.1; 422/50; 422/51; 422/61; 422/129; 422/131; 422/134; 436/8; 436/43; 436/174
(58) Field of Search .................. 422/50, 51, 61, 422/68.1, 129, 131, 134, 135, 138; 436/8, 43, 174

(56) References Cited

U.S. PATENT DOCUMENTS

| | | | |
|---|---|---|---|
| 94,830 | A | 9/1869 | King |
| 1,111,374 | A | 9/1914 | Goddard |
| 1,281,610 | A | 10/1918 | Lundahl |
| 1,841,434 | A | 1/1932 | Gibson |
| 2,025,379 | A | 12/1935 | Croasdale |
| 2,202,860 | A | 6/1940 | McPhee et al. |
| 2,484,391 | A | 10/1949 | Treiss, Jr. |

(List continued on next page.)

FOREIGN PATENT DOCUMENTS

| | | |
|---|---|---|
| CS | 266759 | 6/1990 |
| DE | 198 09 477 | 9/1999 |
| EP | 0529504 A2 | 3/1993 |

(List continued on next page.)

OTHER PUBLICATIONS

Ahrweiler, P. et al., "Automation of Parallel Synthesis From Reagent Preparation Through Sample Workup," Am. Lab. 1997, 29, 12–14.

(List continued on next page.)

Primary Examiner—Jill Warden
Assistant Examiner—Brian Sines
(74) Attorney, Agent, or Firm—Senniger, Powers, Leavitt & Roedel

(57) ABSTRACT

An apparatus and method for carrying out and monitoring the progress and properties of multiple reactions is disclosed. The method and apparatus are especially useful for synthesizing, screening, and characterizing combinatorial libraries, but also offer significant advantages over conventional experimental reactors as well. The apparatus generally includes multiple vessels for containing reaction mixtures, and systems for controlling the stirring rate and temperature of individual reaction mixtures or groups of reaction mixtures. In addition, the apparatus may include provisions for independently controlling pressure in each vessel. In situ monitoring of individual reaction mixtures provides feedback for process controllers, and also provides data for determining reaction rates, product yields, and various properties of the reaction products, including viscosity and molecular weight.

72 Claims, 24 Drawing Sheets

U.S. PATENT DOCUMENTS

| | | |
|---|---|---|
| 2,637,537 A | 5/1953 | Ernst |
| 2,766,022 A | 10/1956 | Bender |
| 2,833,576 A | 5/1958 | Cirone |
| 2,964,511 A | 12/1960 | Cottle |
| 2,991,161 A | 7/1961 | Gasche |
| 2,996,363 A | 8/1961 | Ruyak |
| 3,143,167 A | 8/1964 | Vieth |
| 3,243,165 A | 3/1966 | Woody et al. |
| 3,319,940 A | 5/1967 | Mentnech |
| 3,326,610 A | 6/1967 | Baermann et al. |
| 3,455,540 A | 7/1969 | Marcmann |
| 3,456,923 A | 7/1969 | Zeuzem |
| 3,603,471 A | 9/1971 | Harris, Sr. et al. |
| 3,603,564 A | 9/1971 | Price et al. |
| 3,622,968 A | 11/1971 | Silverman |
| 3,676,653 A | 7/1972 | Arens et al. |
| 3,680,843 A | 8/1972 | Lu et al. |
| 3,693,941 A | 9/1972 | Suchy |
| 3,697,053 A | 10/1972 | Will |
| 3,718,032 A | 2/1973 | Gray |
| 3,778,757 A | 12/1973 | Houston |
| 3,909,647 A | 9/1975 | Peterson |
| 4,037,826 A | 7/1977 | Hulslander et al. |
| 4,048,056 A * | 9/1977 | Romovacek .................. 208/41 |
| 4,065,107 A | 12/1977 | Van Horbek |
| 4,106,825 A | 8/1978 | Ruyak |
| 4,151,400 A | 4/1979 | Smith et al. |
| 4,175,875 A | 11/1979 | Van Horbek |
| 4,195,131 A | 3/1980 | Papas |
| 4,199,265 A | 4/1980 | Sanderson et al. |
| 4,229,110 A | 10/1980 | Lücke |
| 4,235,592 A | 11/1980 | Smith et al. |
| 4,325,914 A | 4/1982 | Ruyak |
| 4,355,906 A | 10/1982 | Ono |
| 4,370,662 A | 1/1983 | Hou et al. |
| 4,391,338 A | 7/1983 | Patashnick et al. |
| 4,438,074 A | 3/1984 | Wilt |
| 4,469,445 A | 9/1984 | Wurtz |
| 4,484,391 A | 11/1984 | Narimatsu |
| 4,506,982 A | 3/1985 | Smithers et al. |
| 4,517,338 A | 5/1985 | Urdea et al. |
| 4,568,195 A | 2/1986 | Herz et al. |
| 4,594,228 A | 6/1986 | Lambert, Jr. et al. |
| 4,598,049 A | 7/1986 | Zelinka et al. |
| 4,640,023 A | 2/1987 | Mori et al. |
| 4,670,404 A | 6/1987 | Swift et al. |
| 4,671,941 A | 6/1987 | Niina et al. |
| 4,675,026 A | 6/1987 | Riemer et al. |
| 4,702,888 A | 10/1987 | Borgialli |
| 4,721,874 A | 1/1988 | Emmert |
| 4,741,200 A | 5/1988 | Hammerle |
| 4,746,490 A | 5/1988 | Saneii |
| 4,748,002 A | 5/1988 | Neimark et al. |
| 4,779,451 A | 10/1988 | Ezawa et al. |
| 4,799,862 A | 1/1989 | Davidson et al. |
| 4,810,099 A | 3/1989 | Langsetmo et al. |
| 4,865,986 A | 9/1989 | Coy et al. |
| 4,901,221 A | 2/1990 | Kodosky et al. |
| 4,910,523 A | 3/1990 | Huguenin et al. |
| 4,919,887 A | 4/1990 | Wakatake |
| 4,924,444 A | 5/1990 | Castellanos |
| 4,924,716 A | 5/1990 | Schneider |
| 4,965,049 A | 10/1990 | Lillig et al. |
| 4,983,046 A | 1/1991 | Murata et al. |
| 5,061,630 A | 10/1991 | Knopf et al. |
| 5,074,671 A | 12/1991 | Roueche et al. |
| 5,098,669 A | 3/1992 | Kawanami et al. |
| 5,117,550 A | 6/1992 | Nadeau et al. |
| 5,143,854 A | 9/1992 | Pirrung et al. |
| 5,145,255 A | 9/1992 | Shimada et al. |
| 5,152,488 A | 10/1992 | Richardson |
| 5,154,891 A | 10/1992 | Brenner |
| 5,191,791 A | 3/1993 | Gerardi et al. |
| 5,201,215 A | 4/1993 | Granstaff et al. |
| 5,217,695 A | 6/1993 | Augustine et al. |
| 5,224,174 A | 6/1993 | Schneider et al. |
| RE34,386 E | 9/1993 | Davidson et al. |
| 5,252,296 A | 10/1993 | Zuckermann et al. |
| 5,255,978 A | 10/1993 | Ibar |
| 5,291,587 A | 3/1994 | Kodosky et al. |
| 5,297,867 A | 3/1994 | Holman |
| 5,304,355 A | 4/1994 | Yant et al. |
| 5,316,728 A | 5/1994 | Hayashi et al. |
| 5,324,483 A | 6/1994 | Cody et al. |
| 5,356,756 A | 10/1994 | Cavicchi et al. |
| 5,357,964 A | 10/1994 | Spivey et al. |
| 5,367,879 A | 11/1994 | Doke et al. |
| 5,375,470 A | 12/1994 | Matsushima et al. |
| 5,380,485 A | 1/1995 | Takahashi et al. |
| 5,380,495 A | 1/1995 | Chang et al. |
| 5,395,594 A | 3/1995 | Nokihara et al. |
| 5,399,014 A | 3/1995 | Takata et al. |
| 5,407,270 A | 4/1995 | Barile et al. |
| 5,437,838 A | 8/1995 | De Moranville et al. |
| 5,439,236 A | 8/1995 | Musil |
| 5,443,791 A | 8/1995 | Cathcart et al. |
| 5,469,369 A | 11/1995 | Rose-Pehrsson et al. |
| 5,499,193 A | 3/1996 | Sugawara et al. |
| 5,503,805 A | 4/1996 | Sugarman et al. |
| 5,515,683 A | 5/1996 | Kessler |
| 5,524,636 A | 6/1996 | Sarvazyan et al. |
| 5,538,694 A | 7/1996 | Delius |
| 5,541,314 A | 7/1996 | McGraw et al. |
| 5,544,489 A | 8/1996 | Moren |
| 5,546,301 A | 8/1996 | Agrawal et al. |
| 5,576,946 A | 11/1996 | Bender et al. |
| 5,593,642 A | 1/1997 | DeWitt et al. |
| 5,593,839 A | 1/1997 | Hubbell et al. |
| 5,601,141 A | 2/1997 | Gordon et al. |
| 5,602,000 A | 2/1997 | Hyman |
| 5,602,756 A | 2/1997 | Atwood et al. |
| 5,609,826 A | 3/1997 | Cargill et al. |
| 5,611,059 A | 3/1997 | Benton et al. |
| 5,639,974 A | 6/1997 | Hanson et al. |
| 5,646,039 A * | 7/1997 | Northrup et al. ........ 435/287.2 |
| 5,651,614 A | 7/1997 | Juneau |
| 5,670,269 A | 9/1997 | Hamada et al. |
| 5,674,742 A | 10/1997 | Northrup et al. |
| 5,697,436 A | 12/1997 | Johnson et al. |
| 5,698,163 A | 12/1997 | Mandel |
| 5,714,127 A | 2/1998 | DeWitt et al. |
| 5,716,584 A | 2/1998 | Baker et al. |
| 5,732,277 A | 3/1998 | Kodosky et al. |
| 5,734,098 A | 3/1998 | Kraus et al. |
| 5,738,439 A | 4/1998 | Flower |
| 5,746,982 A | 5/1998 | Saneii et al. |
| 5,762,881 A | 6/1998 | Harness et al. |
| 5,789,258 A | 8/1998 | Drinkwine et al. |
| 5,802,856 A | 9/1998 | Schaper et al. |
| 5,812,394 A | 9/1998 | Lewis et al. |
| 5,819,842 A | 10/1998 | Potter et al. |
| 5,841,959 A | 11/1998 | Guiremand |
| 5,849,208 A | 12/1998 | Hayes et al. |
| 5,856,101 A | 1/1999 | Hubbell et al. |
| 5,862,052 A | 1/1999 | Nixon et al. |
| 5,866,342 A | 2/1999 | Antonenko et al. |
| 5,869,643 A | 2/1999 | Chatelain et al. |
| 5,871,278 A | 2/1999 | Harry et al. |
| 5,882,601 A | 3/1999 | Kath et al. |
| 5,888,830 A | 3/1999 | Mohan et al. |
| 5,899,567 A | 5/1999 | Morris, Jr. |

| | | |
|---|---|---|
| 5,961,925 A | 10/1999 | Ruediger et al. |
| 5,985,356 A | 11/1999 | Schultz et al. |
| 6,004,617 A | 12/1999 | Schultz et al. |
| 6,030,917 A | 2/2000 | Weinberg et al. |
| 6,045,755 A | 4/2000 | Lebl et al. |
| 6,063,633 A | 5/2000 | Willson, III |
| 6,086,831 A | 7/2000 | Harness et al. |
| 6,109,780 A | 8/2000 | Lesniak |
| 6,132,686 A | 10/2000 | Gallup et al. |

FOREIGN PATENT DOCUMENTS

| | | | |
|---|---|---|---|
| EP | | 0635713 A1 | 1/1995 |
| EP | | 0783922 A1 | 7/1997 |
| EP | | 0796654 A2 | 9/1997 |
| EP | | 0963791 A2 | 12/1999 |
| FR | | 1418757 | 10/1965 |
| FR | | 2630927 | 11/1989 |
| GB | | 989424 | 4/1965 |
| GB | | 1 408 199 | 10/1975 |
| JP | | 10182501 | 7/1988 |
| JP | | 4118424 | 1/1992 |
| SU | | 429064 | 8/1975 |
| WO | WO 95/23329 | | 8/1995 |
| WO | WO 96/14930 | | 5/1996 |
| WO | WO 97/09353 | | 3/1997 |
| WO | WO 98/07026 | | 2/1998 |
| WO | WO 98/07027 | | 2/1998 |
| WO | WO 98/13137 | | 4/1998 |
| WO | WO 98/15501 A2 | | 4/1998 |
| WO | WO 98/15813 | | 4/1998 |
| WO | WO 98/16949 | | 4/1998 |
| WO | WO 98/36826 | | 8/1998 |
| WO | WO 98/39099 | | 9/1998 |
| WO | WO 98/57740 | | 12/1998 |
| WO | WO 99/30817 | | 6/1999 |

OTHER PUBLICATIONS

J.P. Baselt, A. Forster, J. Herrmann and D. Tiebes, Microreactor Technology: Focusing the German Activities in this Novel and Promising Field of Chemical Process Engineering, pp. 13–17, 1997.
Buhlmann, R., et al., "An Open Software Environment to Optimize the Productivity of Robotized Laboratories," J. Chromatogr. Sci. 1994, 32, 243–248.
J.F. Cargill et al., Lab. Rob. Autom., 1996, 8, 139–148.
Cols Corp. About Calorimetry Sciences Corp., www-calscorpt.com/about_csc, Feb. 8, 1999, 3 page.
Corkan, L.A., et al., "Application of an Automated Chemistry Workstation to Problems in Synthetic Chemistry," Chemom. Intell. Lab. Syst. 1992, 17 95–105.
Corkan, A., et al., "Design Concepts for Synthetic Chemistry Workstations," Adv. Lab. Autom. Rob. 1990, 6, 477–497.
Corkan, L. Andrew, Linsey, Johnathan S., Experiment Manager Software for an Automated Chemistry Workstation, Including a Scheduler for Parallel Experimentation, Chemometrics and Intelligent Laboratory Systems: Laboratory Information Management, 17 (1992) 47–74, Elsevier Science Publishers B.V., Amsterdam.
Database WPI, XP002188481, Section Ch, Week 197609, Derwent Publications Ltd., London, GB (Abstract for SU 429 064 A, Kazan Org. Synth. WKS), 1 page.
S. H. Dewitt and A. W. Czarnik, *Combinatiorial Organic Synthesis Using Parke–Davis's Diversomer Method*, Acc. Chem. Res., Mar. 1996, pp. 114–122, vol. 29, American Chemical Society, USA.
Estem Corporation, Heated Reacto—Stations, Oct. 1997.

European Search Report for European Application No. EP 01 11 6443, Jan. 28, 2002, 2 pages.
European Search Report for European Application No. EP 01 11 6442, Feb. 22, 2002, 2 pages.
European Search Report for European Application No. EP 01 11 6411, Feb. 26, 2002, 2 pages.
European Search Report for European Application No. EP 01 11 6401, Mar. 4, 2002, 2 pages.
Gehrer, E., et al., "A Fully Programmable System for the Study of Catalytic Gas Reactions," J. Phys. E: Sci. Instrum. 1985, 18, 10, 836–838.*
Hazard Evaluation Laboratory Inc., High Pressure ChemScan, undated, pp. 2, New Jersey, USA.*
Hazard Evaluation Laboratory Inc., (entire newsletter), HEL Newsletter, at least as early as Mar. 2002, pp. 8, Lawrenceville, New Jersey.*
Hazard Evaluation Laboratory Inc., Process Optimization & Parallel Synthesis, internet address www.helgroup.co.uk/chemscan.cfm, viewed Apr. 17, 2002, pp. 5.*
Hazard Evaluation Laboratory Inc., Complaint with Jury Demand, May 17, 2002, 5 pages, Boston Massachusetts, USA.*
J. Hlavay and G.G. Gullbault, "Applications of the Piezoelectric Crystal Detector in Analytical Chemistry," Analytical Chemistry, vol. 49, No. 13, Nov. 1977.*
K. Keiji Kanazawa and Joseph G. Gordon II, "The Oscillation Frequency of a Quartz Resonator in Contact with a Liquid," vol. 175, pp. 99–105, 1985.*
L. Kiezel et al., Chem. Stosow., 1968, 12, 407–415.*
A.L. Kipling, M. Thompson, "Network Analysis Method Applied to Liquid–Phase Acoustic Wave Sensors", Analytical Chemistry, pp. 1514–1519, vol. 62, 1990.*
J–Kem® Scientific, Inc., "Reaction Blocks" information.*
Josses, P., et al., "Carrying Out Multiple Reactions in Organic Synthesis with a Robot," Adv. Lab. Autom. Rob. 1990, 6, 463–475.*
Li, K.T., et al., Mixing and Control of a CSTR with Series–Parallel Reactions, J. Chin. Inst. Chem. Eng. 1991, 22, 61–69.*
Lindsey, J.S., A Retrospective on the Automation of Laboratory Synthetic Chemistry, Chemom. Intell. Lab. Syst. 1992, 17, 15–45.*
McFarlane, R.C., et al.,"Adaptive Optimizing Control of Multivariable Constrained Chemical Processes. 2. Application Studies," Ind. Eng. Chem. Res. 1989, 28, 1834–1845.
A. Michels, F. Meinen, T. Murdfield, W. Gohde, U.C. Fischer, E. Beckmann and H. Fuch, 1 MHz quartz length extension resonator as a probe for scanning near–field acoustic microscopy, Thin Solid Films, vol. 264, pp. 172–195, 1995.
"MultiReactor—Reactor Block," RoboSynthon, Inc.
H. Muramatsu, K. Kumura, T. Ataka, R. Homma, Y. Miura and I. Karube, A quartz crystal viscocity sensor for monitoring coagulation reaction and its application to a multichannel coagulation detector, Biosensors & Bioelectronics, vol. 6, pp. 353–358, 1991.
J. Nelles et al., Chem. Tech., 1975, 27, 714–716.
T. Nomura and M. Iijima, Electrolytic Determination of Nanomolar Concentration of Silver in Solution with a Piezoelectric Quartz Crystal, Analytica Chimica Acta, vol. 131, pp. 97–102, 1981.
PCT/ISA/220, International Search Report Application No. PCT/US99/18358, Sep. 25, 2000.

Plouvier, J.C., et al., "Experiment Planner for Strategic Experimentation with an Automated Chemistry Workstation," Chemom. Intell. Lab. Syst. 1992, 17–75–94.

Randhava, Ravi, et al., "Advanced Configurations for Catalyst Research," *Chem. Eng. Prog.* Nov. 1983, pp. 52–58, vol. 70, No. 11, American Institute of Chemical Engineers, New York, U.S.

M. Salvet et al., Chem. Abstr. 1997, 126, abstract 200993h.

Takamatsu, T., et al., "Optimal Scheduling and Minimum Storage Tank Capacities in a Process System with Parallel Batch Units," Comput. Chem. Eng. 1979, 3, 185–195.

Eiichi Tamiya and Isao Karube, Computation of Equivalent Circuit Parameters of Quartz Crystals in Contact with Liquids and Study of Liquid Properties, Hiroshi Muramatsu, Analytical Chemistry, vol. 60, pp. 2142–2146, 1988.

Tietz, A., et al., "Temperature Oscillation Calorimetry In Stirred Tank Polymerization Reactors," Dechema Monogr. 1995, 131, 673–680.

S. Vignes et al., Comp. Rend. Congr. Indust., 1961, 405–411.

World Wide Web Argotech.com/quest, May 18, 1998, "Nautilus 2400" information.

World Wide Web Argotech.com/quest, May 18, 1998, "Quest 210" information.

World Wide Web brinkmann.com, 1997, "Brinkman Horizon Stirrers and Hotplace Stirrers" information.

World Wide Web calbay.com, Mar. 31, 1998, "Viscoliner" information.

World Wide Web calscorp.com/about_csc, Feb. 8, 1999, About Calorimeter Sciences Corp. information.

World Wide Web mettler.com, Aug. 10, 1998, "Automatic Laboratory Reactors, Reaction Calorimeters and On–line Analysis" information.

World Wide Web tecan.ch, Jul. 14, 1998, "CAVRO RSP 9000 Robotic Processor" information.

World Wide Web thermometric.com/calorimetry, Jul. 27, 1998, "Calorimetry" information.

Hazard Evaluation Laboratory Inc., *Affordable Reaction Calorimetry: Efficient Process Development and Hazard Assessment*, undated, 4 pages, Herts., England.

Hazard Evaluation Laboratory Inc., *HEL AUTO–LAB: An Automated Reactor and General Purpose Control System*, undated, 4 pages, Monmouth Junction, New Jersey, USA.

Hazard Evaluation Laboratory Inc., *Automated Batch Reactors: Bench Scale With Selected Features*, undated, 4 pages, Monmouth Junction, New Jersey, USA.

Hazard Evaluation Laboratory Inc., *HEL Newsletter*, Summer/Autumn 1993, 4 pages, Herts, England.

Hazard Evaluation Laboratory Inc., *HEL Newsletter*, Autumn/Winter 1999, 4 pages, Issue 7, Monmouth Junction, New Jersey, USA.

Hazard Evaluation Laboratory Inc., *HEL Newsletter*, Spring/Summer 2000, 4 pages, Issue 8, Monmouth Junction, New Jersey, USA.

Hazard Evaluation Laboratory Inc., *HEL Newsletter*, Autumn 2000, 4 pages, Issue 9, Lawrenceville, New Jersey, USA.

Hazard Evaluation Laboratory Inc., *High Pressure Chem-Scan for Rapid Chemical Reaction Scanning*, undated, 2 pages, Lawrenceville, New Jersey, USA.

Hazard Evaluation Laboratory Inc., *Process Development and Safety*, undated, 5 pages, New Jersey, USA.

Hazard Evaluation Laboratory Inc., *Process Development and Safety: Using Computer Controlled Reactors and Calorimeters*, undated, 2 pages, Monmouth Junction, New Jersey, USA.

Hazard Evaluation Laboratory Inc., *Reaction Calorimetry & Laboratory Automation*, undated, 1 page, Herts., England.

Hazard Evaluation Laboratory Inc., *Reaction Calorimetry*, undated, 3 pages.

Hazard Evaluation Laboratory Inc., *Reaction Calorimetry: Simular*, undated, 2 pages, Monmouth Junction, New Jersey, USA.

Hazard Evaluation Laboratory Inc., *Research Scale Reactor Automation: Auto–MATE*, undated, 4 pages, Monmouth Junction, New Jersey, USA.

Hazard Evaluation Laboratory Inc., *Introducing Tips: Tools for Integration of Process Systems*, undated, 1 page, New Jersey, USA.

Hazard Evaluation Laboratory Inc., *Miniature Multiple Reactor System: auto–MATE*, undated, 8 pages, Monmouth Junction, New Jersey, USA.

Hazard Evaluation Laboratory Inc., *Specify SIMULAR Around Your Chemistry*, undated, 5 pages, Lawrenceville, New Jersey, USA.

Hazard Evaluation Laboratory Inc., *First Amended Complaint with Jury Demand*, Jul. 31, 2002, 5 pages, New Jersey, USA.

Hazard Evaluation Laboratory Inc., *Answer to Counterclaim*, Sep. 9, 2002, 3 pages, New Jersey, USA.

Singh, Jasbir, *Thermal Analysis and Reaction Calorimetry*, undated, 3 pages.

Scientific Update, *The Evolution of Revolution: Laboratory Automation in Chemical Process R& D*, Sep. 5, 1997, 3 pages, East Sussex, United Kingdom.

Singh, Jasbir, *Assessing Semi–Batch Reaction Hazards*, The Chemical Engineer, Feb. 25, 1993, 4 pages.

Singh, Jasbir, *Reaction Calorimetry for Process Development: Recent Advances*, Process Safety Progress, Spring 1997, 7 pages.

Singh, Jasbir, *Automation of Reaction Research—An Alternative to Robotics*, European Pharmaceutical Contractor, Nov. 1997, 4 pages.

Singh, Jasbir, *Safe Scaleup of Exothermic Reactions*, Chemical Engineering, May 1997, 4 pages.

Singh, Jasbir, *Scaleable Automated Laboratory Reactors*, undated ("*Scaleable Automated Laboratory Reactors*" title listed in reference 253 noted above), 13 pages, East Sussex, United Kingdom.

Parr Instrument Company, *Stirred Reactors: Series 4520 Options*, undated, 3 pages.

Symyx Technologies, Inc., Answer and Counterclaim, Aug. 30, 2002, 8 pages, New Jersey, USA.

Symyx Technologies, Inc., First Amended Answer and Counterclaim Oct. 30, 2002, 9 pages, New Jersey, USA.

Hazard Evaluation Laboratory Inc., Untitled Drawings, undated, 4 pages.

Waldram, Simon, *Increasing the Scale Process Operations: How to Identify Exothermic Reaction Hazards*, undated, 3 pages.

* cited by examiner

US 6,818,183 B2

MULTI-TEMPERATURE MODULAR REACTOR AND METHOD OF USING SAME

RELATED APPLICATION

The present application is a Continuation-in-Part of U.S. application Ser. No. 09/177,170, filed Oct. 22, 1998, now U.S. Pat. No. 6,548,026 entitled "Parallel Reactor with Internal Sensing and Method of Using Same," which claims the benefit of U.S. Provisional Application No. 60/096,603, filed Aug. 13, 1998. Applicant incorporates the above applications herein by reference and claims priority from these earlier filed applications pursuant to 35 U.S.C. §120.

BACKGROUND

1. Technical Field

The present invention relates to a method and apparatus for rapidly making, screening, and characterizing an array of materials. More particularly, this invention is directed to a multi-temperature reactor for screening and characterizing different zones of materials in a combinatorial library.

2. Discussion

In combinatorial chemistry, a large number of candidate materials are created from a relatively small set of precursors and subsequently evaluated for suitability for a particular application. As currently practiced, combinatorial chemistry permits scientists to systematically explore the influence of structural variations in candidates by dramatically accelerating the rates at which they are created and evaluated. Compared to traditional discovery methods, combinatorial methods sharply reduce the costs associated with preparing and screening each candidate.

Combinatorial chemistry has revolutionized the process of drug discovery. See, for example, 29 Acc. Chem. Res. 1–170 (1996); 97 Chem. Rev. 349–509 (1997); S. Borman, Chem. Eng. News 43–62 (Feb. 24, 1997); A. M. Thayer, Chem. Eng. News 57–64 (Feb. 12, 1996); N. Terret, 1 Drug Discovery Today 402 (1996)). One can view drug discovery as a two-step process: acquiring candidate compounds through laboratory synthesis or through natural products collection, followed by evaluation or screening for efficacy. Pharmaceutical researchers have long used high-throughput screening (HTS) protocols to rapidly evaluate the therapeutic value of natural products and libraries of compounds synthesized and cataloged over many years. However, compared to HTS protocols, chemical synthesis has historically been a slow, arduous process. With the advent of combinatorial methods, scientists can now create large libraries of organic molecules at a pace on par with HTS protocols.

Recently, combinatorial approaches have been used for discovery programs unrelated to drugs. For example, some researchers have recognized that combinatorial strategies also offer promise for the discovery of inorganic compounds such as high-temperature superconductors, magnetoresistive materials, luminescent materials, and catalytic materials. See, for example, co-pending U.S. patent application Ser. No. 08/327,513 "The Combinatorial Synthesis of Novel Materials" (published as WO 96/11878) and co-pending U.S. patent application Ser. No. 08/898,715 "Combinatorial Synthesis and Analysis of Organometallic Compounds and Catalysts" (published as WO 98/03251), which are both herein incorporated by reference.

Because of its success in eliminating the synthesis bottleneck in drug discovery, many researchers have come to narrowly view combinatorial methods as tools for creating structural diversity. Few researchers have emphasized that, during synthesis, variations in temperature, pressure, ionic strength, and other process conditions can strongly influence the properties of library members. For instance, reaction conditions are particularly important in formulation chemistry, where one combines a set of components under different reaction conditions or concentrations to determine their influence on product properties.

Moreover, because the performance criteria in materials science is often different than in pharmaceutical research, many workers have failed to realize that process variables often can be used to distinguish among library members both during and after synthesis. For example, the viscosity of reaction mixtures can be used to distinguish library members based on their ability to catalyze a solution-phase polymerization—at constant polymer concentration, the higher the viscosity of the solution, the greater the molecular weight of the polymer formed. Furthermore, total heat liberated and/or peak temperature observed during an exothermic reaction can be used to rank catalysts.

Therefore, a need exists for an apparatus to rapidly prepare and screen combinatorial libraries in which one can monitor and control process conditions during synthesis and screening.

SUMMARY OF THE INVENTION

In accordance with one aspect of the present invention, there is provided an apparatus for parallel processing of reaction mixtures. The apparatus includes vessels for containing the reaction mixtures, a stirring system, and a temperature control system that is adapted to maintain individual vessels or groups of vessels at different temperatures. The apparatus may consist of a monolithic reactor block, which contains the vessels, or an assemblage of reactor block modules that have individual temperature control devices. A robotic material handling system can be used to automatically load the vessels with starting materials. In addition to heating or cooling individual vessels, the entire reactor block can be maintained at a nearly uniform temperature by circulating a temperature-controlled thermal fluid through channels formed in the reactor block. The stirring system generally includes stirring members—blades, bars, and the like—placed in each of the vessels, and a mechanical or magnetic drive mechanism. Torque and rotation rate can be controlled and monitored through strain gages, phase lag measurements, and speed sensors.

The apparatus may optionally include a system for evaluating material properties of the reaction mixtures. The system includes mechanical oscillators located within the vessels. When stimulated with a variable-frequency signal, the mechanical oscillators generate response signals that depend on properties of the reaction mixture. Through calibration, mechanical oscillators can be used to monitor molecular weight, specific gravity, elasticity, dielectric constant, conductivity, and other material properties of the reaction mixtures.

In accordance with a second aspect of the present invention, there is provided an apparatus for monitoring rates of production or consumption of a gas-phase component of a reaction mixture. The apparatus generally comprises a closed vessel for containing the reaction mixture, a stirring system, a temperature control system and a pressure control system. The pressure control system includes a pressure sensor that communicates with the vessel, as well as a valve that provides venting of a gaseous product from the vessel. In addition, in cases where a gas-phase reactant is consumed during reaction, the valve provides access to a source of the reactant. Pressure monitoring of the vessel, coupled with venting of product or filling with reactant allows the investigator to determine rates of production or consumption, respectively.

In accordance with a third aspect of the present invention, there is provided an apparatus for monitoring rates of consumption of a gas-phase reactant. The apparatus generally comprises a closed vessel for containing the reaction mixture, a stirring system, a temperature control system and a pressure control system. The pressure control system includes a pressure sensor that communicates with the vessel, as well as a flow sensor that monitors the flow rate of reactant entering the vessel. Rates of consumption of the reactant can be determined from the reactant flow rate and filling time.

In accordance with a fourth aspect of the present invention, there is provided a method of making and characterizing a plurality of materials. The method includes the steps of providing vessels with starting materials to form reaction mixtures, confining the reaction mixtures in the vessels to allow reaction to occur, and stirring the reaction mixtures for at least a portion of the confining step. The method further includes the step of evaluating the reaction mixtures by tracking at least one characteristic of the reaction mixtures for at least a portion of the confining step. Various characteristics or properties can be monitored during the evaluating step, including temperature, rate of heat transfer, conversion of starting materials, rate of conversion, torque at a given stirring rate, stall frequency, viscosity, molecular weight, specific gravity, elasticity, dielectric constant, and conductivity.

In accordance with a fifth aspect of the present invention, there is provided a method of monitoring the rate of consumption of a gas-phase reactant. The method comprises the steps of providing a vessel with starting materials to form the reaction mixture, confining the reaction mixtures in the vessel to allow reaction to occur, and stirring the reaction mixture for at least a portion of the confining step. The method further includes filling the vessel with the gas-phase reactant until gas pressure in the vessel exceeds an upper-pressure limit, $P_H$, and allowing gas pressure in the vessel to decay below a lower-pressure limit, $P_L$. Gas pressure in the vessel is monitored and recorded during the addition and consumption of the reactant. This process is repeated at least once, and rates of consumption of the gas-phase reactant in the reaction mixture are determined from the pressure versus time record.

In accordance with a sixth aspect of the present invention, there is provided a method of monitoring the rate of production of a gas-phase product. The method comprises the steps of providing a vessel with starting materials to form the reaction mixture, confining the reaction mixtures in the vessel to allow reaction to occur, and stirring the reaction mixture for at least a portion of the confining step. The method also comprises the steps of allowing gas pressure in the vessel to rise above an upper-pressure limit, $P_H$, and venting the vessel until gas pressure in the vessel falls below a lower-pressure limit, $P_L$. The gas pressure in the vessel is monitored and recorded during the production of the gas-phase component and subsequent venting of the vessel. The process is repeated at least once, so rates of production of the gas-phase product can be calculated from the pressure versus time record.

A further understanding of the nature and advantages of the present invention may be realized by reference to the remaining portions of the specification and the drawings.

DETAILED DESCRIPTION OF THE PREFERRED EMBODIMENTS

The present invention provides an apparatus and method for carrying out and monitoring the progress and properties of multiple reactions. It is especially useful for synthesizing, screening, and characterizing combinatorial libraries, but offers significant advantages over conventional experimental reactors as well. For example, in situ monitoring of individual reaction mixtures not only provides feedback for process controllers, but also provides data for determining reaction rates, product yields, and various properties of the reaction products, including viscosity and molecular weight. Moreover, in situ monitoring coupled with tight process control can improve product selectivity, provide opportunities for process and product optimization, allow processing of temperature-sensitive materials, and decrease experimental variability. Other advantages result from using small mixture volumes. In addition to conserving valuable reactants, decreasing sample size increases surface area relative to volume within individual reactor vessels. This improves the uniformity of reaction mixtures, aids gas-liquid exchange in multiphase reactions, and increases heat transfer between the samples and the reactor vessels. Because large samples respond much slower to changes in system conditions, the use of small samples, along with in situ monitoring and process control, also allows for time-dependent processing and characterization.

Overview of Parallel Reactor

Figure 1:
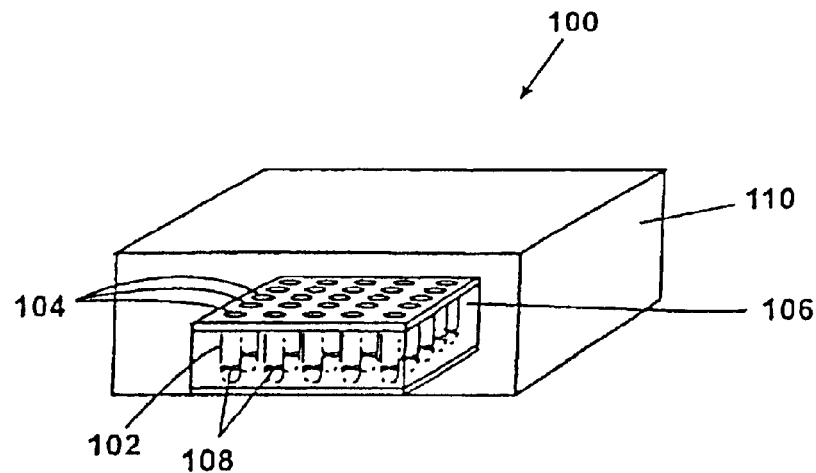
FIG. 1 illustrates a parallel reactor system in accordance with the present invention.

FIG. 1 shows one embodiment of a parallel reactor system 100. The reactor system 100 includes removable vessels 102 for receiving reactants. Wells 104 formed into a reactor block 106 contain the vessels 102. Although the wells 104 can serve as reactor vessels, removable vessels 102 or liners provide several advantages. For example, following reaction and preliminary testing (screening), one can remove a subset of vessels 102 from the reactor block 106 for further in-depth characterization. When using removable vessels 102, one can also select vessels 102 made of material appropriate for a given set of reactants, products, and reaction conditions. Unlike the reactor block 106, which represents a significant investment, the vessels 102 can be discarded if damaged after use. Finally, one can lower system 100 costs and ensure compatibility with standardized sample preparation and testing equipment by designing the reactor block 106 to accommodate commercially available vessels.

As shown in FIG. 1, each of the vessels 102 contains a stirring blade 108. In one embodiment, each stirring blade 108 rotates at about the same speed, so that each of the reaction mixtures within the vessels 102 experience similar mixing. Because reaction products can be influenced by mixing intensity, a uniform rotation rate ensures that any differences in products does not result from mixing variations. In another embodiment, the rotation rate of each stirring blade 108 can be varied independently, which as discussed below, can be used to characterize the viscosity and molecular weight of the reaction products to or can be used to study the influence of mixing speed on reaction.

Depending on the nature of the starting materials, the types of reactions, and the method used to characterize reaction products and rates of reaction, it may be desirable to enclose the reactor block 106 in a chamber 110. The chamber 110 may be evacuated or filled with a suitable gas. In some cases, the chamber 110 may be used only during the loading of starting materials into the vessels 102 to minimize contamination during sample preparation, for example, to prevent poisoning of oxygen sensitive catalysts. In other cases, the chamber 110 may be used during the reaction process or the characterization phase, providing a convenient method of supplying one or more gases to all of the vessels 102 simultaneously. In this way, a gaseous reactant can be added to all of the vessels 102 at one time. Note, however, it is often necessary to monitor the rate of disappearance of a gaseous reactant—for example, when determining rates of conversion—and in such cases the vessels 102 are each sealed and individually connected to a gas source, as discussed below.

Figure 2:
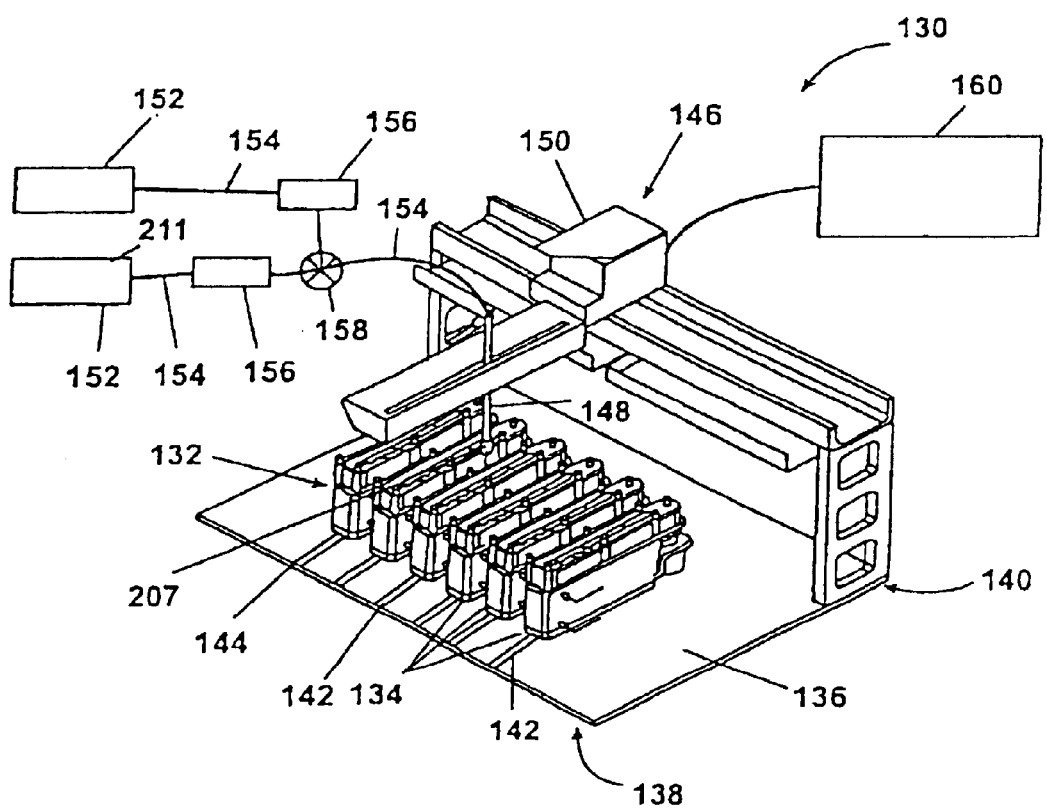
FIG. 2 shows a perspective view of a modular reactor block with a robotic liquid handling system.

FIG. 2 shows a perspective view of a parallel reactor system 130 comprised of a modular reactor block 132. The modular reactor block 132 shown in FIG. 2 consists of six modules 134, and each module 134 contains eight vessels (not shown). Note, however, the number of modules 134 and the number of vessels within each of the modules 134 can vary.

The use of modules 134 offers several advantages over a monolithic reactor block. For example, the size of the reactor block 132 can be easily adjusted depending on the number of reactants or the size of the combinatorial library. Also, relatively small modules 134 are easier to handle, transport, and fabricate than a single, large reactor block. A damaged module can be quickly replaced by a spare module, which minimizes repair costs and downtime. Finally, the use of modules 134 improves control over reaction parameters. For instance, stirring speed, temperature, and pressure of each of the vessels can be varied between modules.

In the embodiment shown in FIG. 2, each of the modules 134 is mounted on a base plate 136 having a front 138 and a rear 140. The modules 134 are coupled to the base plate 136 using guides (not shown) that mate with channels 142 located on the surface of the base plate 136. The guides prevent lateral movement of the modules 134, but allow linear travel along the channels 142 that extend from the front 138 toward the rear 140 of the base plate 136. Stops 144 located in the channels 142 near the front 138 of the base plate 136 limit the travel of the modules 134. Thus, one or more of the modules 134 can be moved towards the front 138 of the base plate 136 to gain access to individual vessels while the other modules 134 undergo robotic filling. In another embodiment, the modules 134 are rigidly mounted to the base plate 136 using bolts, clips, or other fasteners.

As illustrated in FIG. 2, a conventional robotic material handling system 146 is ordinarily used to load vessels with starting materials. The robotic system 146 includes a pipette or probe 148 that dispenses measured amounts of liquids into each of the vessels. The robotic system 146 manipulates the probe 148 using a 3-axis translation system 150. The probe 148 is connected to sources 152 of liquid reagents through flexible tubing 154. Pumps 156, which are located along the flexible tubing 154, are used to transfer liquid reagents from the sources 152 to the probe 148. Suitable pumps 156 include peristaltic pumps and syringe pumps. A multi-port valve 158 located downstream of the pumps 156 selects which liquid reagent from the sources 152 is sent to the probe 148 for dispensing in the vessels.

The robotic liquid handling system 146 is controlled by a processor 160. In the embodiment shown in FIG. 2, the user first supplies the processor 160 with operating parameters using a software interface. Typical operating parameters include the coordinates of each of the vessels and the initial compositions of the reaction mixtures in individual vessels. The initial compositions can be specified as lists of liquid reagents from each of the sources 152, or as incremental additions of various liquid reagents relative to particular vessels.

Temperature Control and Monitoring

The ability to monitor and control the temperature of individual reactor vessels is an important aspect of the present invention. During synthesis, temperature can have a profound effect on structure and properties of reaction products. For example, in the synthesis of organic molecules, yield and selectivity often depend strongly on temperature. Similarly, in polymerization reactions, polymer structure and properties—molecular weight, particle size, monomer conversion, microstructure—can be influenced by reaction temperature. During screening or characterization of combinatorial libraries, temperature control and monitoring of library members is often essential to making meaningful comparisons among members. Finally, temperature can be used as a screening criteria or can be used to calculate useful process and product variables. For instance, catalysts of exothermic reactions can be ranked based on peak reaction temperature and/or total heat released over the course of reaction, and temperature measurements can be used to compute rates of reaction and conversion.

Figure 3:
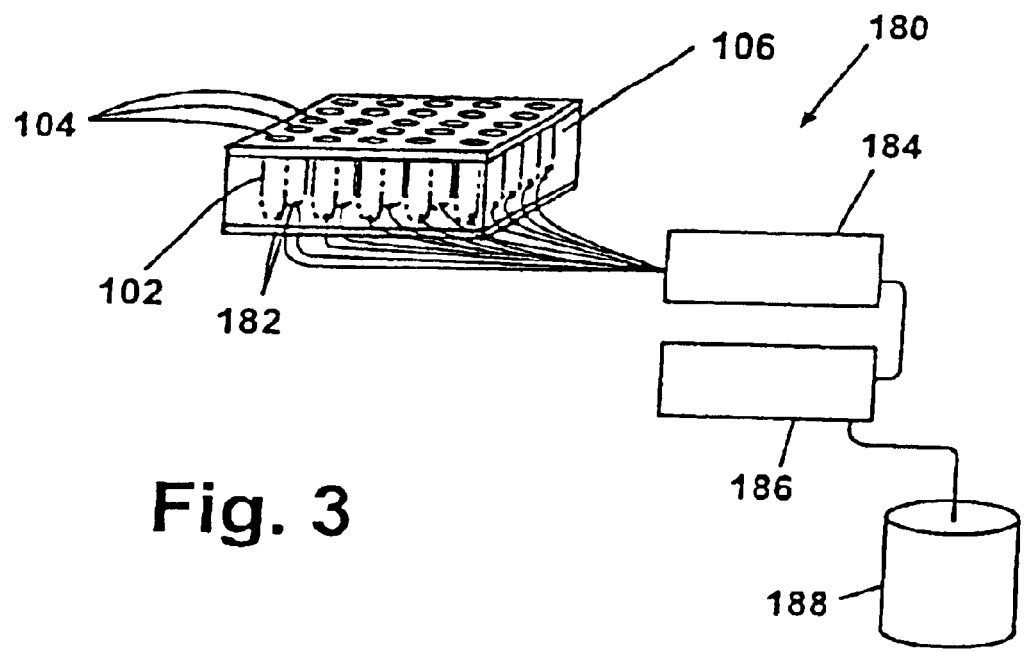
FIG. 3 shows a temperature monitoring system.

FIG. 3 illustrates one embodiment of a temperature monitoring system 180, which includes temperature sensors 182 that are in thermal contact with individual vessels 102. For clarity, we describe the temperature monitoring system 180 with reference to the monolithic reactor block 106 of FIG. 1, but this disclosure applies equally well to the modular reactor block 132 of FIG. 2. Suitable temperature sensors 182 include jacketed or non-jacketed thermocouples (TC), resistance thermometric devices (RTD), and thermistors. The temperature sensors 182 communicate with a temperature monitor 184, which converts signals received from the temperature sensors 182 to a standard temperature scale. An optional processor 186 receives temperature data from the temperature monitor 184. The processor 186 performs calculations on the data, which may include wall corrections and simple comparisons between different vessels 102, as well as more involved processing such as calorimetry calculations discussed below. During an experimental run, temperature data is typically sent to storage 188 so that it can be retrieved at a later time for analysis.

Figure 4:
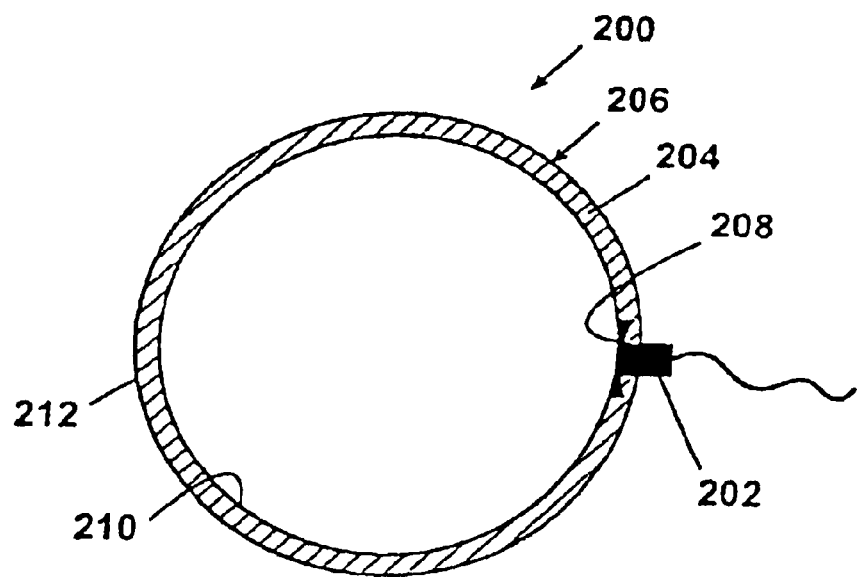
FIG. 4 shows a cross-sectional view of an integral temperature sensor-vessel assembly.

FIG. 4 shows a cross-sectional view of an integral temperature sensor-vessel assembly 200. The temperature sensor 202 is embedded in the wall 204 of a reactor vessel 206. The surface 208 of the temperature sensor 202 is located adjacent to the inner wall 210 of the vessel to ensure good thermal contact between the contents of the vessel 206 and the temperature sensor 202. The sensor arrangement shown in FIG. 3 is useful when it is necessary to keep the contents of the reactor vessel 206 free of obstructions. Such a need might arise, for example, when using a freestanding mixing device, such as a magnetic stirring bar. Note, however, that fabricating an integral temperature sensor such as the one shown in FIG. 4 can be expensive and time consuming, especially when using glass reactor vessels.

Thus, in another embodiment, the temperature sensor is immersed in the reaction mixture. Because the reaction environment within the vessel may rapidly damage the temperature sensor, it is usually jacketed with an inert material, such as a fluorinated thermoplastic. In addition to low cost, direct immersion offers other advantages, including rapid response and improved accuracy. In still another embodiment, the temperature sensor is placed on the outer surface 212 of the reactor vessel of FIG. 4. As long as the thermal conductivity of the reactor vessel is known, relatively accurate and rapid temperature measurements can be made.

Figure 5:
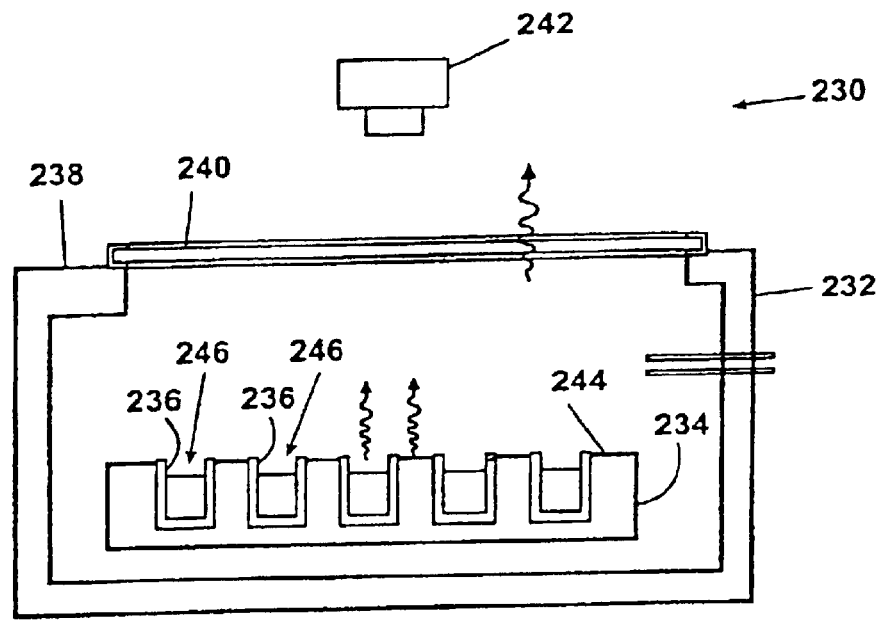
FIG. 5 shows a side view of an infrared temperature measurement system.

One can also remotely monitor temperature using an infrared system illustrated in FIG. 5. The infrared monitoring system 230 comprises an optional isolation chamber 232, which contains the reactor block 234 and vessels 236. The top 238 of the chamber 232 is fitted with a window 240 that is transparent to infrared radiation. An infrared-sensitive camera 242 positioned outside the isolation chamber 232, detects and records the intensity of infrared radiation passing through the window 240. Since infrared emission intensity depends on source temperature, it can be used to distinguish high temperature vessels from low temperature vessels. With suitable calibration, infrared intensity can be converted to temperature, so that at any given time, the camera 242 provides "snapshots" of temperature along the surface 244 of the reactor block 234. In the embodiment shown in FIG. 5, the tops 246 of the vessels 236 are open. In an alternate embodiment, the tops 246 of the vessels 236 are fitted with infrared transparent caps (not shown). Note that, with stirring, the temperature is uniform within a particular vessel, and therefore the surface temperature of the vessel measured by infrared emission will agree with the bulk temperature measured by a TC or RTD immersed in the vessel.

The temperature of the reactor vessels and block can be controlled as well as monitored. Depending on the application, each of the vessels can be maintained at the same temperature or at different temperatures during an experiment. For example, one may screen compounds for catalytic activity by first combining, in separate vessels, each of the compounds with common starting materials; these mixtures are then allowed to react at uniform temperature. One may then further characterize a promising catalyst by combining it in numerous vessels with the same starting materials used in the screening step. The mixtures then react at different temperatures to gauge the influence of temperature on catalyst performance (speed, selectivity). In many instances, it may be necessary to change the temperature of the vessels during processing. For example, one may decrease the temperature of a mixture undergoing a reversible exothermic reaction to maximize conversion. Or, during a characterization step, one may ramp the temperature of a reaction product to detect phase transitions (melting range, glass transition temperature). Finally, one may maintain the reactor block at a constant temperature, while monitoring temperature changes in the vessels during reaction to obtain calorimetric data as described below.

Figure 6:
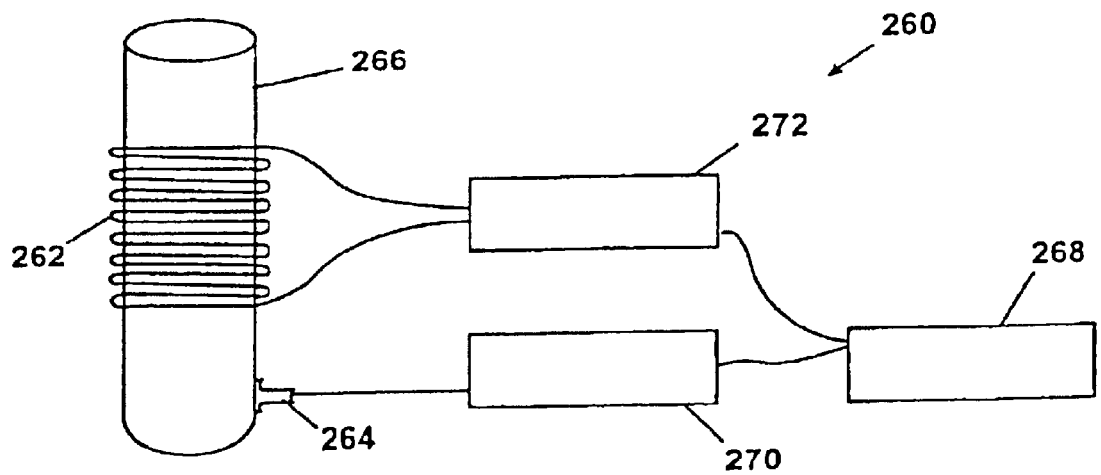
FIG. 6 shows a temperature monitoring and control system for a reactor vessel.

FIG. 6 shows a useful temperature control system 260, which comprises separate heating 262 and temperature sensing 264 elements. The heating element 262 shown in FIG. 6 is a conventional thin filament resistance heater whose heat output is proportional to the product of the filament resistance and the square of the current passing through the filament. The heating element 262 is shown coiled around a reactor vessel 266 to ensure uniform radial and axial heating of the vessel 266 contents. The temperature sensing element 264 can be a TC, RTD, and the like. The heating element 262 communicates with a processor 268, which based on information received from the temperature sensor 264 through a temperature monitoring system 270, increases or decreases heat output of the heating element 262. A heater control system 272, located in the communication path between the heating element 262 and the processor 268, converts a processor 268 signal for an increase (decrease) in heating into an increase (decrease) in electrical current through the heating element 262. Generally, each of the vessels 104 of the parallel reactor system 100 shown in FIG. 1 or FIG. 3 are equipped with a heating element 262 and one or more temperature sensors 264, which communicate with a central heater control system 272, temperature monitoring system 270, and processor 268, so that the temperature of the vessels 104 can be controlled independently.

Other embodiments include placing the heating element 262 and temperature sensor 264 within the vessel 266, which results in more accurate temperature monitoring and control of the vessel 266 contents, and combining the temperature sensor and heating element in a single package. A thermistor is an example of a combined temperature sensor and heater, which can be used for both temperature monitoring and control because its resistance depends on temperature.

Figure 7:
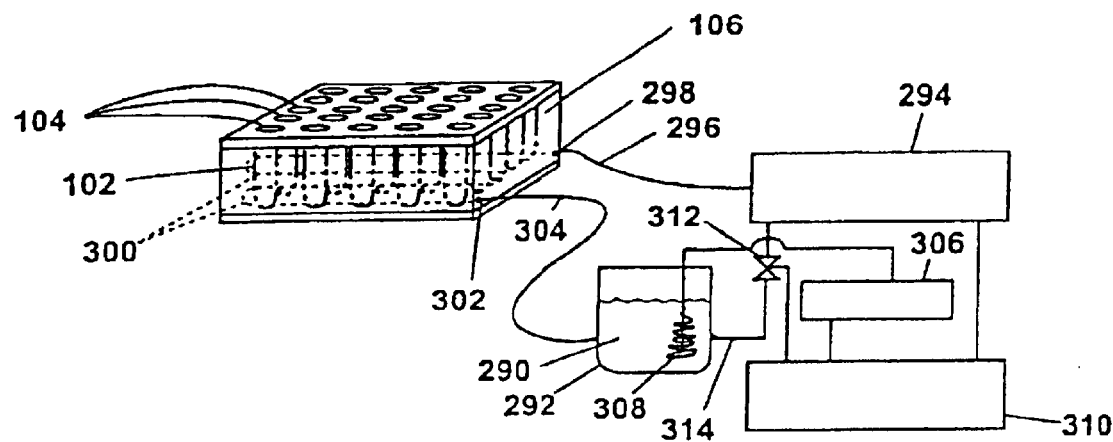
FIG. 7 illustrates another temperature control system, which includes liquid cooling and heating of the reactor block.
Figure 8:
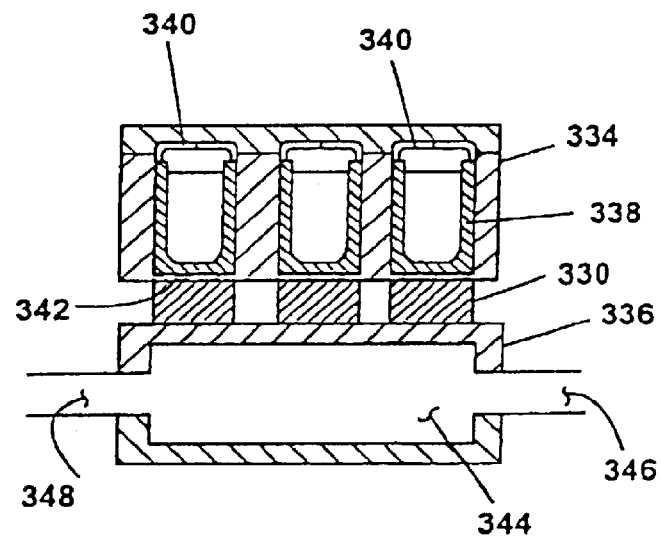
FIG. 8 is a cross-sectional view of thermoelectric devices sandwiched between a reactor block and heat transfer plate.

FIG. 7 illustrates another temperature control system, which includes liquid cooling and heating of the reactor block 106. Regulating the temperature of the reactor block 106 provides many advantages. For example, it is a simple way of maintaining nearly uniform temperature in all of the reactor vessels 102. Because of the large surface area of the vessels 102 relative to the volume of the reaction mixture, cooling the reactor block 106 also allows one to carryout highly exothermic reactions. When accompanied by temperature control of individual vessels 102, active cooling of the reactor block 106 allows for processing at sub-ambient temperatures. Moreover, active heating or cooling of the reactor block 106 combined with temperature control of individual vessels 102 or groups of vessels 102 also decreases response time of the temperature control feedback. One may control the temperature of individual vessels 102 or groups of vessels 102 using compact heat transfer devices, which include electric resistance heating elements or thermoelectric devices, as shown in FIG. 6 and FIG. 8, respectively. Although we describe reactor block cooling with reference to the monolithic reactor block 106, one may, in a like manner, independently heat or cool individual modules 134 of the modular reactor block 132 shows in FIG. 2.

Returning to FIG. 7, a thermal fluid 290, such as water, steam, a silicone fluid, a fluorocarbon, and the like, is transported from a uniform temperature reservoir 292 to the reactor block 106 using a constant or variable speed pump 294. The thermal fluid 290 enters the reactor block 106 from a pump outlet conduit 296 through an inlet port 298. From the inlet port 298, the thermal fluid 290 flows through a passageway 300 formed in the reactor block 106. The passageway may comprise single or multiple channels. The passageway 300 shown in FIG. 7, consists of a single channel that winds its way between rows of vessels 102, eventually exiting the reactor block 106 at an outlet port 302. The thermal fluid 290 returns to the reservoir 292 through a reactor block outlet conduit 304. A heat pump 306 regulates the temperature of the thermal fluid 290 in the reservoir 292 by adding or removing heat through a heat transfer coil 308. In response to signals from temperature sensors (not shown) located in the reactor block 106 and the reservoir 292, a processor 310 adjusts the amount of heat added to or removed from the thermal fluid 290 through the coil 308. To adjust the flow rate of thermal fluid 290 through the passageway 300, the processor 310 communicates with a valve 312 located in a reservoir outlet conduit 314. The reactor block 106, reservoir 292, pump 294, and conduits 296, 304, 314 can be insulated to improve temperature control in the reactor block 106.

Because the reactor block 106 is typically made of a metal or other material possessing high thermal conductivity, the single channel passageway 300 is usually sufficient for maintaining the temperature of the block 106 a few degrees above or below room temperature. To improve temperature uniformity within the reactor block 106, the passageway can be split into parallel channels (not shown) immediately downstream of the inlet port 298. In contrast to the single channel passageway 300 depicted in FIG. 7, each of the parallel channels passes between a single row of vessels 102 before exiting the reactor block 106. This parallel flow arrangement decreases the temperature gradient between the inlet 298 and outlet 302 ports. To further improve temperature uniformity and heat exchange between the vessels 102 and the block 106, the passageway 300 can be enlarged so that the wells 104 essentially project into a cavity containing the thermal fluid 290. Additionally, one may eliminate the reactor block 106 entirely, and suspend or immerse the vessels 102 in a bath containing the thermal fluid 290.

FIG. 8 illustrates the use of thermoelectric devices for heating and cooling individual vessels. Thermoelectric devices can function as both heaters and coolers by reversing the current flow through the device. Unlike resistive heaters, which convert electric power to heat, thermoelectric devices are heat pumps that exploit the Peltier effect to transfer heat from one face of the device to the other. A typical thermoelectric assembly has the appearance of a sandwich, in which the front face of the thermoelectric device is in thermal contact with the object to be cooled (heated), and the back face of the device is in thermal contact with a heat sink (source). When the heat sink or source is ambient air, the back face of the device typically has an array of thermally conductive fins to increase the heat transfer area. Preferably, the heat sink or source is a liquid. Compared to air, liquids have higher thermal conductivity and heat capacity, and therefore should provide better heat transfer through the back face of the device. But, because thermoelectric devices are usually made with bare metal connections, they often must be physically isolated from the liquid heat sink or source.

For example, FIG. 8 illustrates one way of using thermoelectric devices 330 to heat and cool reactor vessels 338 using a liquid heat sink or source. In the configuration shown in FIG. 8, thermoelectric devices 330 are sandwiched between a reactor block 334 and a heat transfer plate 336. Reactor vessels 338 sit within wells 340 formed in the reactor block 334. Thin walls 342 at the bottom of the wells 340, separate the vessels 338 from the thermoelectric devices 330, ensuring good thermal contact. As shown in FIG. 8, each of the vessels 338 thermally contacts a single thermoelectric device 330, although in general, a thermoelectric device can heat or cool more than one of the vessels 338. The thermoelectric devices 330 either obtain heat from, or dump heat into, a thermal fluid that circulates through an interior cavity 344 of the heat transfer plate 336. The thermal fluid enters and leaves the heat transfer plate 336 through inlet 346 and outlet 348 ports, and its temperature is controlled in a manner similar to that shown in FIG. 7. During an experiment, the temperature of the thermal fluid is typically held constant, while the temperature of the vessels 338 is controlled by adjusting the electrical current, and hence, the heat transport through the thermoelectric devices 330. Though not shown in FIG. 8, the temperature of the vessels 338 are controlled in a manner similar to the scheme depicted in FIG. 6. Temperature sensors located adjacent to the vessels 338 and within the heat transfer plate cavity 344 communicate with a processor via a temperature monitor. In response to temperature data from the temperature monitor, the processor increases or decrease heat flow to or from the thermoelectric devices 330. A thermoelectric device control system, located in the communication path between the thermoelectric devices 330 and the processor, adjusts the magnitude and direction of the flow of electrical current through each of the thermoelectric devices 330 in response to signals from the processor.

Calorimetric Data Measurement and Use

Temperature measurements often provide a qualitative picture of reaction kinetics and conversion and therefore can be used to screen library members. For example, rates of change of temperature with respect to time, as well as peak temperatures reached within each of the vessels can be used to rank catalysts. Typically, the best catalysts of an exothermic reaction are those that, when combined with a set of reactants, result in the greatest heat production in the shortest amount of time.

In addition to its use as a screening tool, temperature measurement—combined with proper thermal management and design of the reactor system—can also be used to obtain quantitative calorimetric data. From such data, scientists can, for example, compute instantaneous conversion and reaction rate, locate phase transitions (melting point, glass transition temperature) of reaction products, or measure latent heats to deduce structural information of polymeric materials, including degree of crystallinity and branching.

Figure 9:
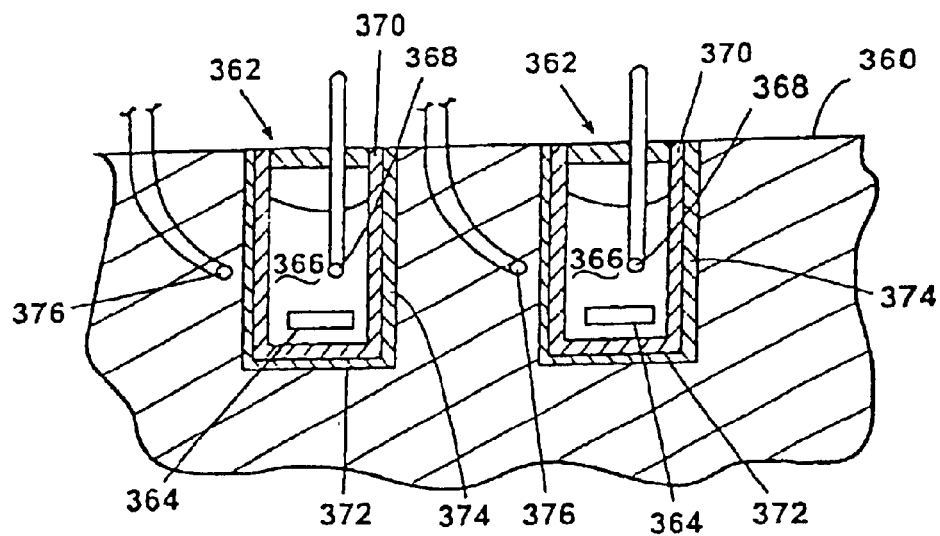
FIG. 9 is a cross-sectional view of a portion of a reactor block useful for obtaining calorimetric data.

FIG. 9 shows a cross-sectional view of a portion of a reactor block 360 that can be used to obtain accurate calorimetric data. Each of the vessels 362 contain stirring blades 364 to ensure that the contents 366 of the vessels 362 are well mixed and that the temperature within any one of the vessels 362, $T_j$, is uniform. Each of the vessels 362 contains a thermistor 368, which measures $T_j$ and heats the vessel contents 366. The walls 370 of the vessels 362 are made of glass, although one may use any material having relatively low thermal conductivity, and similar mechanical strength and chemical resistance. The vessels 362 are held within wells 372 formed in the reactor block 360, and each of the wells 372 is lined with an insulating material 374 to further decrease heat transfer to or from the vessels 362. Useful insulating materials 374 include glass wool, silicone rubber, and the like. The insulating material 374 can be eliminated or replaced by a thermal paste when better thermal contact between that reactor block 360 and the vessels 362 is desired—good thermal contact is needed, for example, when investigating exothermic reactions under isothermal conditions. The reactor block 360 is made of a material having high thermal conductivity, such as aluminum, stainless steel, brass, and so on. High thermal conductivity, accompanied by active heating or cooling using any of the methods described above, help maintain uniform temperature, $T_u$, throughout the reactor block 360. One can account for non-uniform temperatures within the reactor block 360 by measuring $T_{oj}$, the temperature of the block 360 in the vicinity of each of the vessels 362, using block temperature sensors 376. In such cases, $T_{oj}$, instead of $T_u$, is used in the calorimetric calculations described next.

An energy balance around the contents 366 of one of the vessels 362 (jth vessel) yields an expression for fractional conversion, $X_j$, of a key reactant at any time, t, assuming that the heat of reaction, $\Delta H_{rj}$ and the specific heat of the vessel contents 366, $C_{Pj}$, are known and are constant over the temperature range of interest:

$$M_j c_{P,j} \frac{dT_j}{dt} = m_{o,j}\Delta H_{r,j}\frac{dX_j}{dt} + Q_{in,j} - Q_{out,j}. \quad \text{I}$$

In expression I, $M_j$ is the mass of the contents 366 of the jth vessel; $m_{o,j}$ is the initial mass of the key reactant; $Q_{in,j}$ is the rate of heat transfer into the jth vessel by processes other than reaction, as for example, by resistance heating of the thermistor 368. $Q_{out,j}$ is the rate of heat transfer out of the jth vessel, which can be determined from the expression:

$$Q_{out,j} = U_j A_j (T_j - T_o) = U_j A_j \Delta T_j \quad \text{II}$$

where $A_j$ is the heat transfer area—the surface area of the jth vessel—and $U_j$ is the heat transfer coefficient, which depends on the properties of the vessel 362 and its contents 366, as well as the stirring rate. $U_j$ can be determined by measuring the temperature rise, $\Delta T_j$, in response to a known heat input.

Equations I and II can be used to determine conversion from calorimetric data in at least two ways. In a first method, the temperature of the reactor block 360 is held constant, and sufficient heat is added to each of the vessels 362 through the thermistor 368 to maintain a constant value of $\Delta T_j$. Under such conditions, and after combining equations I and II, the conversion can be calculated from the expression $$X_j = \frac{1}{m_{o,j}\Delta H_{r,j}}\left(U_j A_j t_f \Delta T_j - \int_0^{t_f} Q_{in,j} dt\right), \quad \text{III}$$

where the integral can be determined by numerically integrating the power consumption of the thermistor 368 over the length of the experiment, $t_f$. This method can be used to measure the heat output of a reaction under isothermal conditions.

In a second method, the temperature of the reactor block 360 is again held constant, but $T_j$ increases or decreases in response to heat produced or consumed in the reaction. Equation I and II become under such circumstances $$X_j = \frac{1}{m_{o,j}\Delta H_{r,j}}\left(M_j c_{P,j}(T_{f,j} - T_{i,j}) + U_j A_j \int_0^{t_f}\Delta T_j dt\right. \quad \text{IV}$$

In equation IV, the integral can be determined numerically, and $T_{fj}$ and $T_{ij}$ are temperatures of the reaction mixture within the jth vessel at the beginning and end of reaction, respectively. Thus, if $T_{ij}$ equals $T_{ij}$, the total heat liberated is proportional to $$\int_0^{\tau_f} \Delta T_j dt.$$

This method is simpler to implement than the isothermal method since it does not require temperature control of individual vessels. But, it can be used only when the temperature change in each of the reaction vessels 362 due to reaction does not significantly influence the reaction under study.

One may also calculate the instantaneous rate of disappearance of the key reactant in the jth vessel, $-r_j$, using equation I, III or IV since $-r$ is related to conversion through the relationship $$-r_j = C_{o,j} \frac{dX_j}{dt}, \qquad \text{V}$$

which is valid for constant volume reactions. The constant $C_{oj}$ is the initial concentration of the key reactant.

Stirring Systems

Mixing variables such as stirring blade torque, rotation rate, and geometry, may influence the course of a reaction and therefore affect the properties of the reaction products. For example, the overall heat transfer coefficient and the rate of viscous dissipation within the reaction mixture may depend on the stirring blade rate of rotation. Thus, in many instances it is important that one monitor and control the rate of stirring of each reaction mixture to ensure uniform mixing. Alternatively, the applied torque may be monitored in order to measure the viscosity of the reaction mixture. As described in the next section, measurements of solution viscosity can be used to calculate the average molecular weight of polymeric reaction products.

Figure 10:
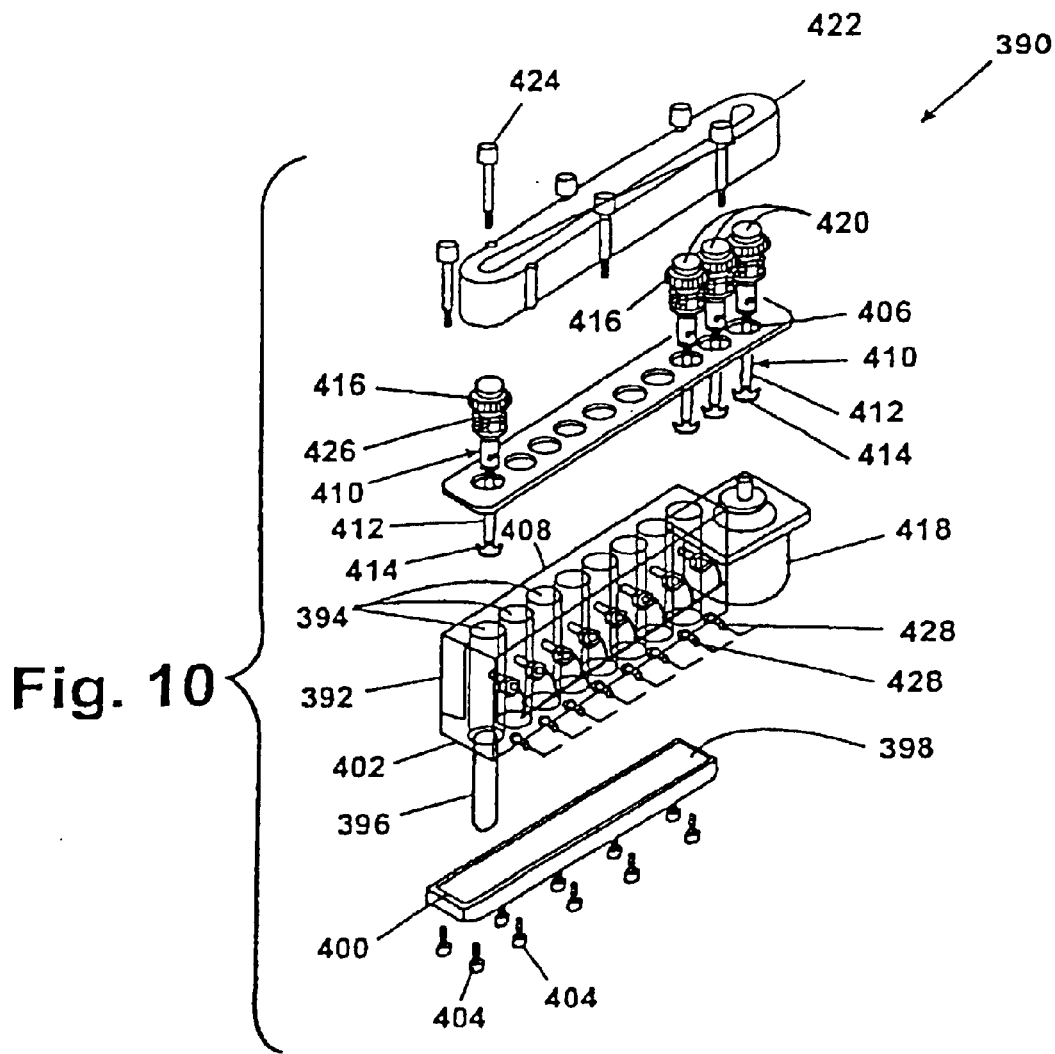
FIG. 10 is an exploded perspective view of a stirring system for a single module of a modular reactor block of the type shown in FIG. 2.

FIG. 10 shows an exploded, perspective view of a stirring system for a single module 390 of a modular reactor block of the type shown in FIG. 2. The module 390 comprises a block 392 having eight wells 394 for containing removable reaction vessels 396. The number of wells 394 and reaction vessels 396 can vary. The top surface 398 of a removable lower plate 400 serves as the base for each of the wells 394 and permits removal of the reaction vessels 396 through the bottom 402 of the block 392. Screws 404 secure the lower plate 400 to the bottom 402 of the block 392. An upper plate 406, which rests on the top 408 of the block 392, supports and directs elongated stirrers 410 into the interior of the vessels 396. Each of the stirrers 410 comprises a spindle 412 and a rotatable stirring member or stirring blade 414 which is attached to the lower end of each spindle 412. A gear 416 is attached to the upper end of each of each spindle 412. When assembled, each gear 416 meshes with an adjacent gear 416 forming a gear train (not shown) so that each stirrer 410 rotates at the same speed. A DC stepper motor 418 provides torque for rotating the stirrers 410, although an air-driven motor, a constant-speed AC motor, or a variable-speed AC motor can be used instead. A pair of driver gears 420 couple the motor 418 to the gear train. A removable cover 422 provides access to the gear train, which is secured to the block 392 using threaded fasteners 424. In addition to the gear train, one may employ belts, chains and sprockets, or other drive mechanisms. In alternate embodiments, each of the stirrers 410 are coupled to separate motors so that the speed or torque of each of the stirrers 410 can be independently varied and monitored. Furthermore, the drive mechanism—whether employing a single motor and gear train or individual motors—can be mounted below the vessels 362. In such cases, magnetic stirring blades placed in the vessels 362 are coupled to the drive mechanism using permanent magnets attached to gear train spindles or motor shafts.

In addition to the stirring system, other elements shown in FIG. 10 merit discussion. For example, the upper plate 406 may contain vessel seals 426 that allow processing at pressures different than atmospheric pressure. Moreover, the seals 426 permit one to monitor pressure in the vessels 396 over time. As discussed below, such information can be used to calculate conversion of a gaseous reactant to a condensed species. Note that each spindle 412 may penetrate the seals 426, or may be magnetically coupled to an upper spindle member (not shown) attached to the gear 416. FIG. 10 also shows temperature sensors 428 embedded in the block 392 adjacent to each of the wells 394. The sensors 428 are part of the temperature monitoring and control system described previously.

In another embodiment, an array of electromagnets rotate freestanding stirring members or magnetic stirring bars, which obviates the need for the mechanical drive system shown in FIG. 10. Electromagnets are electrical conductors that produce a magnetic field when an electric current passes through them. Typically, the electrical conductor is a wire coil wrapped around a solid core made of material having relatively high permeability, such as soft iron or mild steel.

Figure 11:
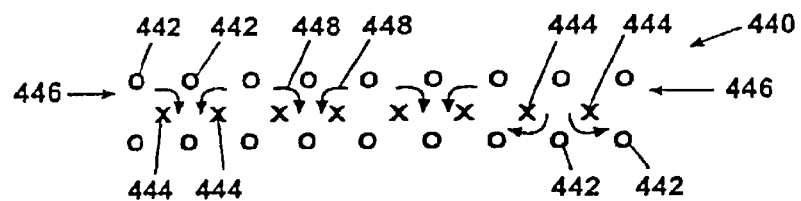
FIG. 11 is a schematic representation of an electromagnetic stirring system.

FIG. 11 is a schematic representation of one embodiment of an electromagnet stirring array 440. The electromagnets 442 or coils belonging to the array 440 are mounted in the lower plate 400 of the reactor module 390 of FIG. 10 so that their axes are about parallel to the centerlines of the vessels 396. Although greater magnetic field strength can be achieved by mounting the electromagnets with their axes perpendicular to the centerlines of the vessels 396, such a design is more difficult to implement since it requires placing electromagnets between the vessels 396. The eight crosses or vessel sites 444 in FIG. 11 mark the approximate locations of the respective centers of each of the vessels 396 of FIG. 10 and denote the approximate position of the rotation axes of the magnetic stirring bars (not shown). In the array 440 shown in FIG. 1, four electromagnets 442 surround each vessel site 444, though one may use fewer or greater numbers of electromagnets 442. The minimum number of electromagnets per vessel site is two, but in such a system it is difficult to initiate stirring, and it is common to stall the stirring bar. Electromagnet size and available packing density primarily limit the maximum number of electromagnets.

Figure 12:
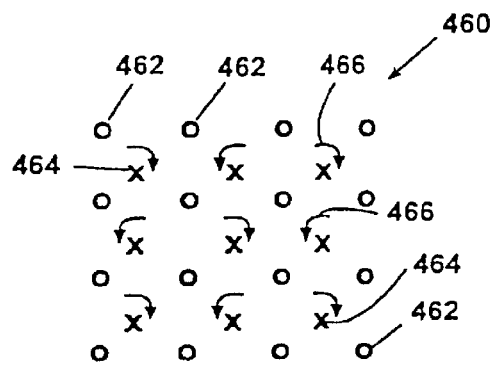
FIGS. 12–13 are schematic representations of portions of electromagnet stirring arrays in which the ratios of electromagnets to vessel sites approach 1:1 and 2:1, respectively, as the number of vessel sites becomes large.
Figure 13:
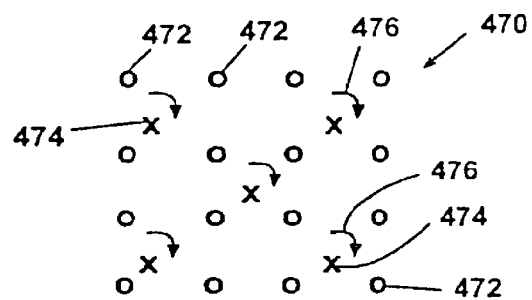

As illustrated in FIG. 11, each vessel site 444, except those at the ends 446 of the array 440, shares its four electromagnets 442 with two adjacent vessel sites. Because of this sharing, magnetic stirring bars at adjacent vessel sites rotate in opposite directions, as indicated by the curved arrows 448 in FIG. 11, which may lead to stalling. Other array configurations are possible. For example, FIG. 12 shows a portion of an array 460 in which the ratio of electromagnets 462 to vessel sites 464 approaches 1:1 as the number of vessel sites 464 becomes large. Because each of the vessel sites 464 shares its electromagnets 462 with its neighbors, magnetic stirring bars at adjacent vessel sites rotate in opposite directions, as shown by curved arrows 466. In contrast, FIG. 13 shows a portion of an array 470 in which the ratio of electromagnets 472 to vessel sites 474 approaches 2:1 as the number of vessel sites becomes large.

Figure 14:
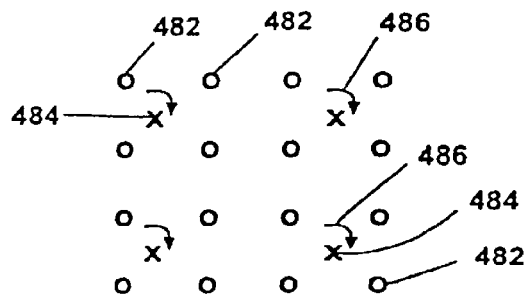
FIG. 14 is a schematic representation of an electromagnet stirring array in which the ratio of electromagnets to vessel sites is 4:1.

Because of the comparatively large number of electromagnets 472 to vessel sites 474, all of the magnetic stirring bars can be made to rotate in the same direction 476, which minimizes stalling. Similarly, FIG. 14 shows an array 480 in which the number of electromagnets 482 to vessel sites 484 is 4:1. Each magnetic stirring bar rotates in the same direction 486.

Figure 15:
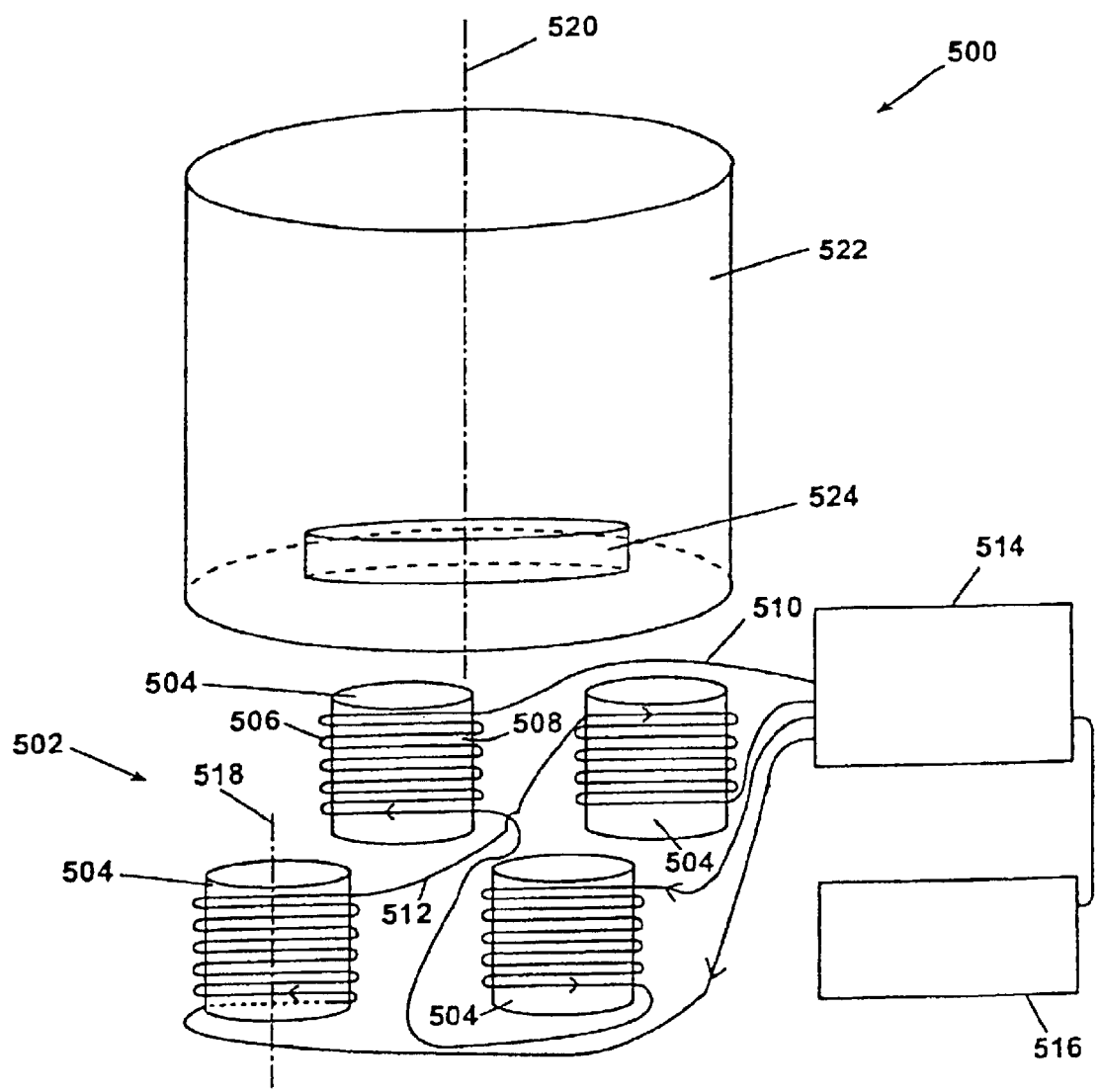
FIG. 15 shows additional elements of an electromagnetic stirring system, including drive circuit and processor.

FIG. 15 illustrates additional elements of an electromagnetic stirring system 500. For clarity, FIG. 15 shows a square electromagnet array 502 comprised of four electromagnets 504, although larger arrays, such as those shown in FIGS. 12–14, can be used. Each of the electromagnets 504 comprises a wire 506 wrapped around a high permeability solid core 508. The pairs of electromagnets 504 located on the two diagonals of the square array 502 are connected in series to form a first circuit 510 and a second circuit 512. The first 510 and second 512 circuits are connected to a drive circuit 514, which is controlled by a processor 516. Electrical current, whether pulsed or sinusoidal, can be varied independently in the two circuits 510, 512 by the drive circuit 514 and processor 516. Note that within each circuit 510, 512, the current flows in opposite directions in the wire 506 around the core 508. In this way, each of the electromagnets 504 within a particular circuit 510, 512 have opposite magnetic polarities. The axes 518 of the electromagnets 504 are about parallel to the centerline 520 of the reactor vessel 522. A magnetic stirring bar 524 rests on the bottom of the vessel 522 prior to operation. Although the electromagnets 504 can also be oriented with their axes 518 perpendicular to the vessel centerline 520, the parallel alignment provides higher packing density.

Figure 16:
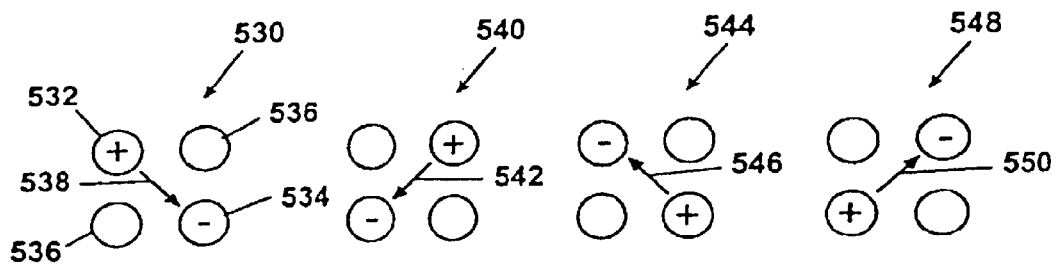
FIG. 16 illustrates the magnetic field direction of a 2×2 electromagnet array at four different times during one rotation of a magnetic stirring bar.

FIG. 16 shows the magnetic field direction of a 2×2 electromagnet array at four different times during one full rotation of the magnetic stirring bar 524 of FIG. 15, which is rotating at a steady frequency of $\omega$ radians·s$^{-1}$. In FIG. 16, a circle with a plus sign 532 indicates that the electromagnet produces a magnetic field in a first direction; a circle with a minus sign 534 indicates that the electromagnet produces a magnetic field in a direction opposite to the first direction; and a circle with no sign 536 indicates that the electromagnet produces no magnetic field. At time t=0, the electromagnets 530 produce an overall magnetic field with a direction represented by a first arrow 538 at the vessel site. At time $$t = \frac{\pi}{2\omega},$$

the electromagnets 540 produce an overall magnetic field with a direction represented by a second arrow 542. Since the magnetic stirring bar 524 (FIG. 15) attempts to align itself with the direction of the overall magnetic field, it rotates clockwise ninety degrees from the first direction 538 to the second direction 542. At time $$t = \frac{\pi}{\omega},$$

the electromagnets 544 produce an overall magnetic field with a direction represented by a third arrow 546. Again, the magnetic stirring bar 524 aligns itself with the direction of the overall magnetic field, and rotates clockwise an additional ninety degrees. At time $$t = \frac{3\pi}{2\omega},$$

the electromagnets 548 produce an overall magnetic field with a direction represented by a fourth arrow 550, which rotates the magnetic stirring bar 524 clockwise another ninety degrees. Finally, at time $$t = \frac{2\pi}{\omega},$$

the electromagnets 530 produce an overall magnetic field with direction represented by the first arrow 538, which rotates the magnetic stirring bar 524 back to its position at time t=0.

Figure 17:
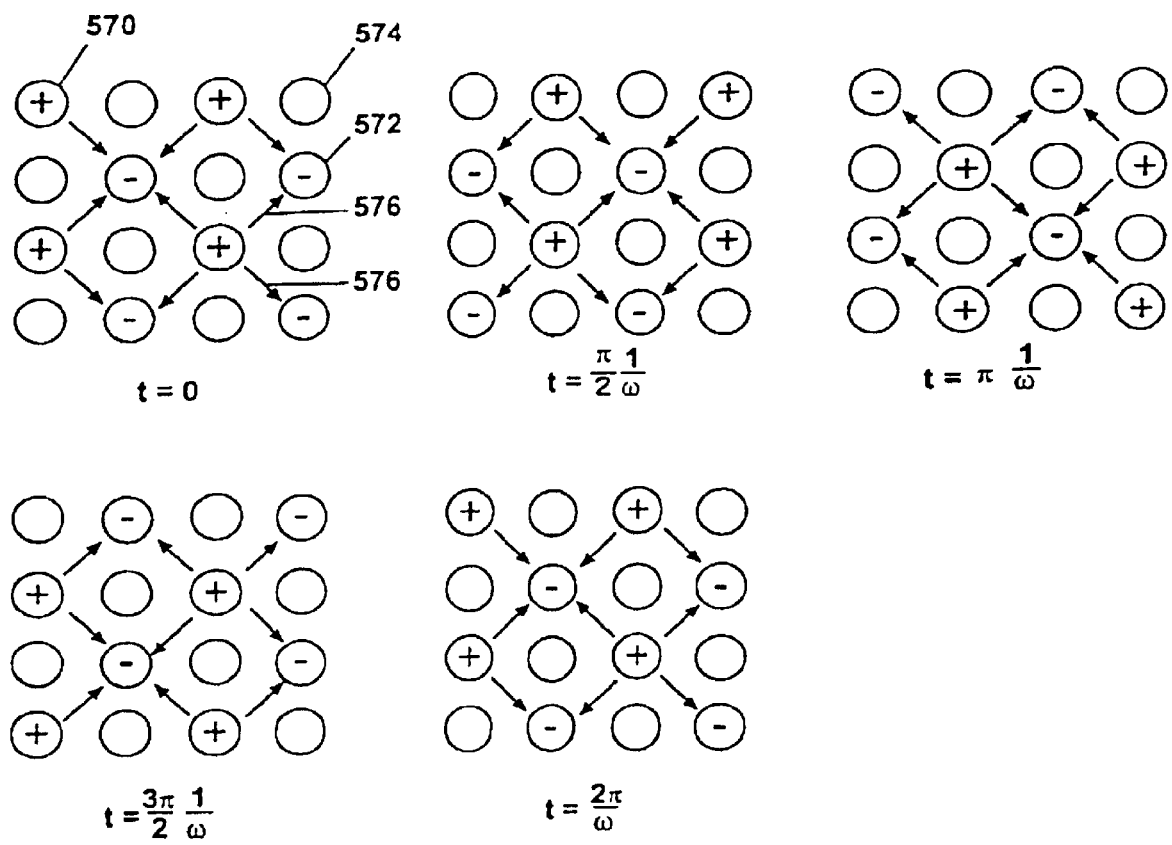
FIG. 17 illustrates the magnetic field direction of a 4×4 electromagnet array at five different times during one full rotation of a 3×3 array of magnetic stirring bars.
Figure 18:
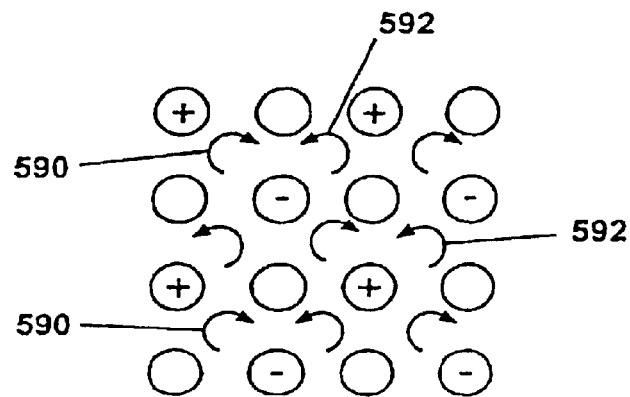
FIG. 18 illustrates the rotation direction of the 3×3 array of magnetic stirring bars shown in FIG. 17.

FIG. 17 illustrates magnetic field direction of a 4×4 electromagnetic array at five different times during one full rotation of a 3×3 array of magnetic stirring bars. As in FIG. 15, a circle with a plus sign 570, a minus sign 572, or no sign 574 represents the magnetic field direction of an individual electromagnet, while an arrow 576 represents the direction of the overall magnetic field at a vessel site. As shown, sixteen electromagnets are needed to rotate nine magnetic stirring bars. But, as indicated in FIG. 18, due to sharing of electromagnets by multiple magnetic stirring bars, the rotational direction of the magnetic fields is non-uniform. Thus, five of the fields rotate in a clockwise direction 590 while the remaining four fields rotate in a counter-clockwise direction 592.

Figure 19:
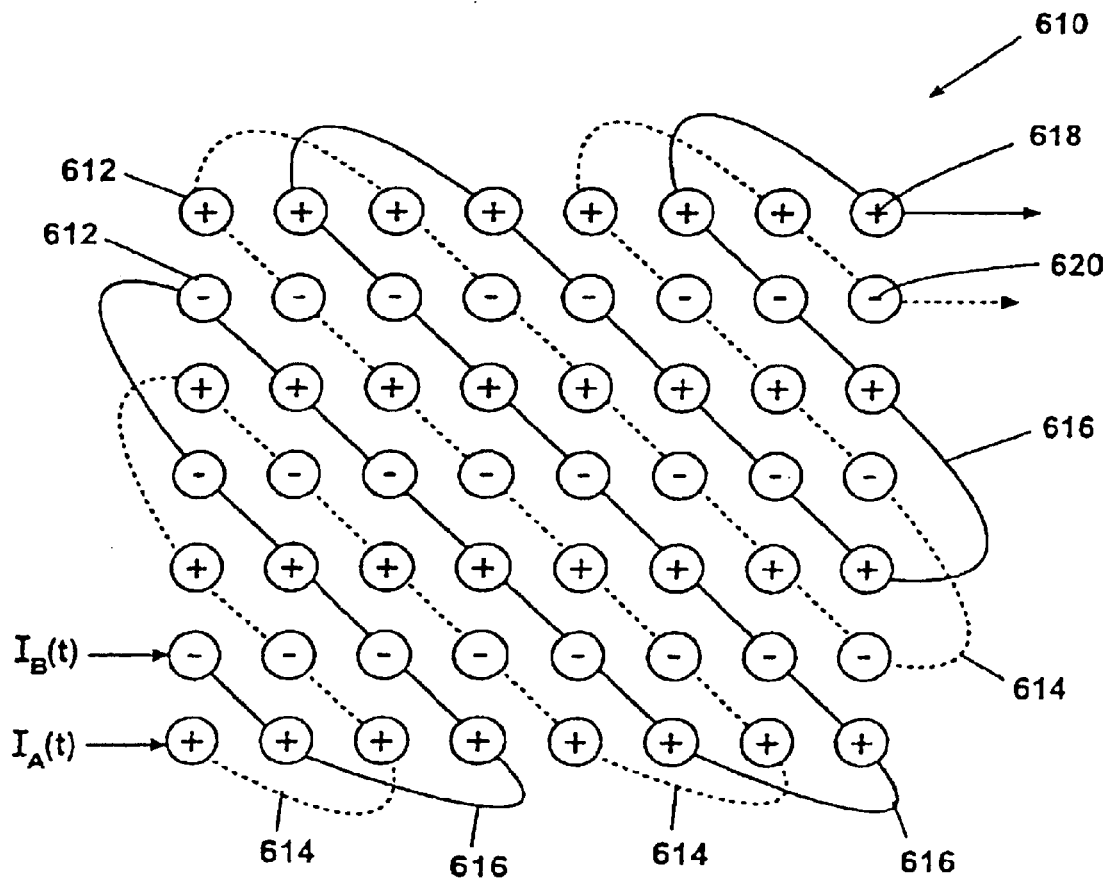
FIG. 19 shows a wiring configuration for an electromagnetic stirring system.
Figure 20:
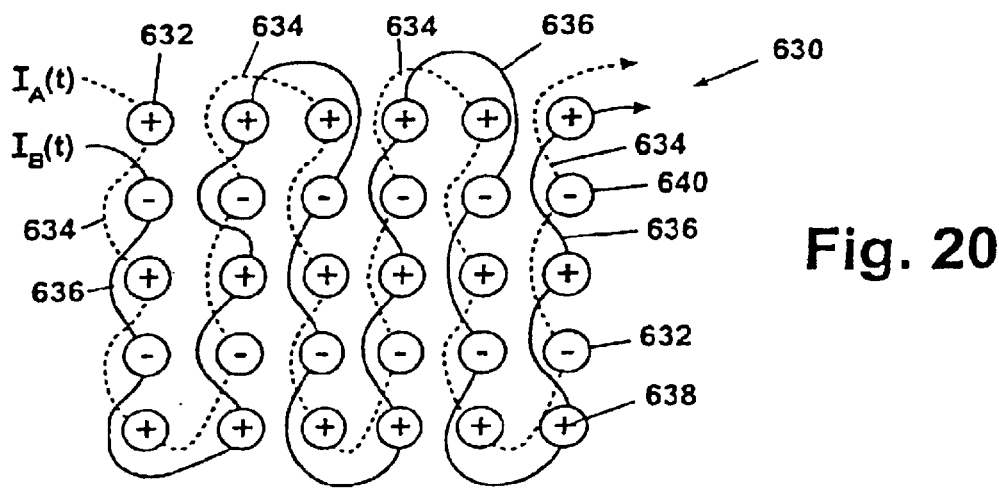
FIG. 20 shows an alternate wiring configuration for an electromagnetic stirring system.

FIG. 19 and FIG. 20 illustrate wiring configurations for electromagnet arrays in which each vessel site is located between four electromagnets defining four corners of a quadrilateral sub-array. For each vessel site, both wiring configurations result in an electrical connection between electromagnets located on the diagonals of a given sub-array. In the wiring configuration 610 shown in FIG. 19, electromagnets 612 in alternating diagonal rows are wired together to form two series of electromagnets 612. Dashed and solid lines represent electrical connections between electromagnets 612 in a first series 614 and a second series 616, respectively. Plus signs 618 and minus signs 620 indicate polarity (magnetic field direction) of individual electromagnets 612 at any time, t, when current in the first series 614 and the second series 616 of electromagnets 612 are in phase. FIG. 20 illustrates an alternate wiring configuration 630 of electromagnets 632, where again, dashed and solid lines represent electrical connections between the first 634 and second series 636 of electromagnets 632, and plus signs 638 and minus signs 640 indicate magnetic polarity.

Note that for both wiring configurations 610, 630, the polarities of the electromagnets 612, 632 of the first series 614, 634 are not the same, though amplitudes of the current passing through the connections between the electromagnets 612, 632 of the first series 614, 634 are equivalent. The same is true for the second series 616, 636 of electromagnets 612, 632. One can achieve opposite polarities within the first series 614, 634 or second series 616, 636 of electromagnets 612, 632 by reversing the direction of electrical current around the core of the electromagnet 612, 632. See, for example, FIG. 15. In the two wiring configurations 610, 630 of FIGS. 19 and 20, every quadrilateral array of four adjacent electromagnets 612, 632 defines a site for rotating a magnetic stirring bar, and the diagonal members of each of the four adjacent electromagnets 612, 632 belong to the first series 614, 634 and the second 616, 636 series of electromagnets 612, 632. Moreover, within any set of four adjacent electromagnets 612, 632, each pair of electromagnets 612, 632 belonging to the same series have opposite polarities. The two wiring configurations 610, 630 of FIGS. 19 and 20 can be used with any of the arrays 460, 470, 480 shown in FIGS. 12–14.

The complex wiring configurations 610, 630 of FIGS. 19 and 20 can be placed on a printed circuit board, which serves as both a mechanical support and alignment fixture for the electromagnets 612, 632. The use of a printed circuit board allows for rapid interconnection of the electromagnets 612, 632, greatly reducing assembly time and cost, and eliminating wiring errors associated with manual soldering of hundreds of individual connections. Switches can be used to turn stirring on and off for individual rows of vessels. A separate drive circuit may be used for each row of vessels, which allows stirring speed to be used as a variable during an experiment.

Figure 21:
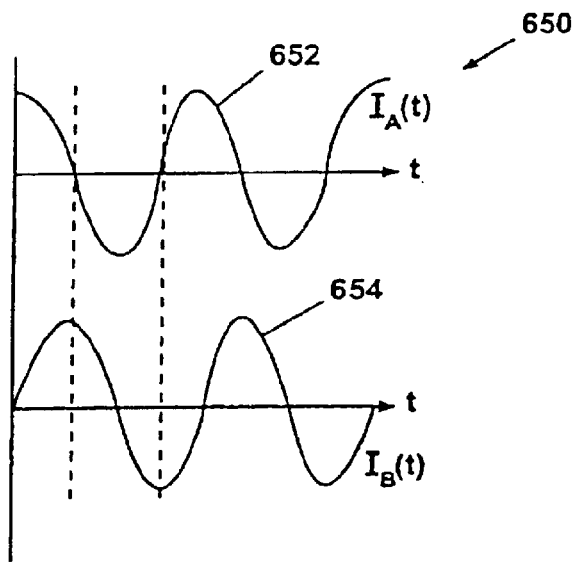
FIG. 21 shows the phase relationship between sinusoidal source currents, $I_A(t)$ and $I_B(t)$, which drive two series of electromagnets shown in FIGS. 19 and 20.

FIG. 21 is a plot 650 of current versus time and shows the phase relationship between sinusoidal source currents, $I_A(t)$ 652 and $I_B(t)$ 654, which drive, respectively, the first series 614, 634 and the second series 616, 636 of electromagnets 612, 632 shown in FIGS. 19 and 20. The two source currents 652, 654 have equivalent peak amplitude and frequency, $\omega_o$, though $I_A(t)$ 652 lags $I_B(t)$ 654 by $$\frac{\pi}{2}$$

radians. Because of this phase relationship, magnetic stirring bars placed at rotation sites defined by any four adjacent electromagnets 612, 632 of FIGS. 19 and 20 will each rotate at an angular frequency of $\omega_o$, though adjacent stirring bars will rotate in opposite directions when the electromagnet array 460 depicted in FIG. 12 is used. If, however, the arrays 470, 480 shown in FIGS. 13 and 14 are used, adjacent stirring bars will rotate in the same direction. In an alternate embodiment, a digital approximation to a sine wave can be used.

Figure 22:
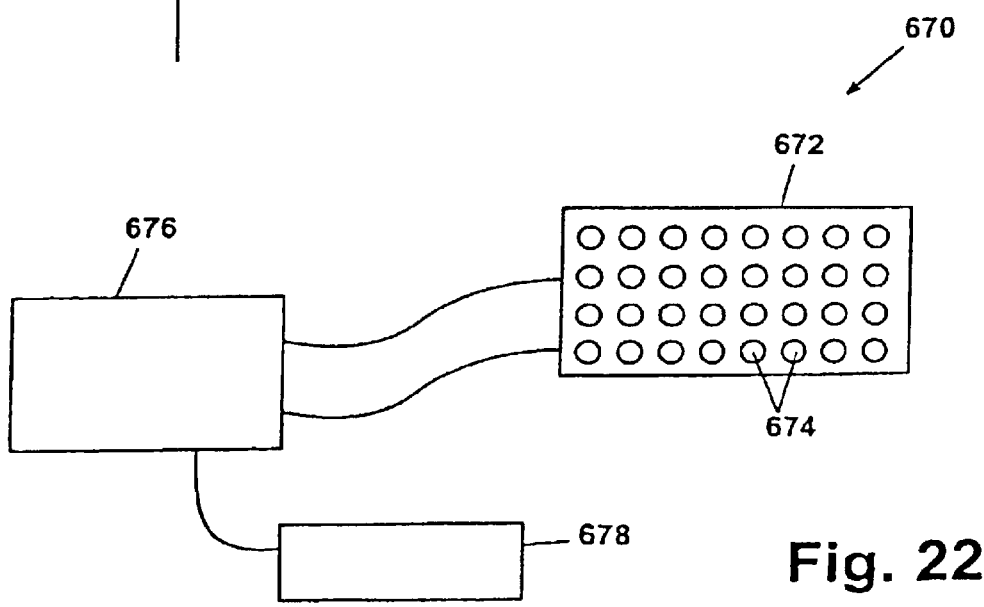
FIG. 22 is a block diagram of a power supply for an electromagnetic stirring system.

FIG. 22 is a block diagram of a power supply 670 for an electromagnet array 672. Individual electromagnets 674 are wired together in a first and second series as, for example, shown in FIG. 19 or 20. The first and second series of electromagnets 674 are connected to a power source 676, which provides the two series with sinusoidal driving currents that are $$\frac{\pi}{2}$$

radians out of phase. Normally, the amplitudes of the two driving currents are the same and do not depend on frequency. A processor 678 controls both the amplitude and the frequency of the driving currents.

Viscosity and Related Measurements

The present invention provides for in situ measurement of viscosity and related properties. As discussed below, such data can be used, for example, to monitor reactant conversion, and to rank or characterize materials based on molecular weight or particle size.

The viscosity of a polymer solution depends on the molecular weight of the polymer and its concentration in solution. For polymer concentrations well below the "semidilute limit"—the concentration at which the solvated polymers begin to overlap one another—the solution viscosity, $\eta$, is related to the polymer concentration, C, in the limit as C approaches zero by the expression $$\eta = (1 + C[\eta])\eta_S \quad \text{VI}$$

where $\eta_S$ is the viscosity of the solvent. Essentially, adding polymer to a solvent increases the solvent's viscosity by an amount proportional to the polymer concentration. The proportionality constant $[\eta]$, is known as the intrinsic viscosity, and is related to the polymer molecular weight, M, through the expression $$[\eta] = [\eta_0]M^\alpha, \quad \text{VII}$$

where $[\eta_0]$ and $\alpha$ are empirical constants. Equation VII is known as the Mark-Houwink-Sakurda (MHS) relation, and it, along with equation VI, can be used to determine molecular weight from viscosity measurements.

Equation VI requires concentration data from another source; with polymerization reactions, polymer concentration is directly related to monomer conversion. In the present invention, such data can be obtained by measuring heat evolved during reaction (see equation III and IV) or, as described below, by measuring the amount of a gaseous reactant consumed during reaction. The constants in the MHS relation are functions of temperature, polymer composition, polymer conformation, and the quality of the polymer-solvent interaction. The empirical constants, $[\eta_0]$ and $\alpha$, have been measured for a variety of polymer-solvent pairs, and are tabulated in the literature.

Although equations VI and VII can be used to approximate molecular weight, in situ measurements of viscosity in the present invention are used mainly to rank reaction products as a function of molecular weight. Under most circumstances, the amount of solvent necessary to satisfy the concentration requirement of equation VI would slow the rate of reaction to an unacceptable level. Therefore, most polymerizations are carried out at polymer concentrations above the semidilute limit, where the use of equations VI and VII to calculate molecular weight would lead to large error. Nevertheless, viscosity can be used to rank reaction products even at concentrations above the semidilute limit since a rise in viscosity during reaction generally reflects an increase in polymer concentration, molecular weight or both. If necessary, one can accurately determine molecular weight from viscosity measurements at relatively high polymer concentration by first preparing temperature-dependent calibration curves that relate viscosity to molecular weight. But the curves would have to be obtained for every polymer-solvent pair produced, which weighs against their use for screening new polymeric materials.

In addition to ranking reactions, viscosity measurements can also be used to screen or characterize dilute suspensions of insoluble particles—polymer emulsions or porous supports for heterogeneous catalysts—in which viscosity increases with particle size at a fixed number concentration. In the case of polymer emulsions, viscosity can serve as a measure of emulsion quality. For example, solution viscosity that is constant over long periods of time may indicate superior emulsion stability, or viscosity within a particular range may correlate with a desired emulsion particle size. With porous supports, viscosity measurements can be used to identify active catalysts: in many cases, the catalyst support will swell during reaction due to the formation of insoluble products within the porous support.

In accordance with the present invention, viscosity or related properties of the reactant mixtures are monitored by measuring the effect of viscous forces on stirring blade rotation. Viscosity is a measure of a fluid's resistance to a shear force. This shear force is equal to the applied torque, $\Gamma$, needed to maintain a constant angular velocity of the stirring blade. The relationship between the viscosity of the reaction mixture and the applied torque can be expressed as $$\Gamma = K_\omega(\omega, T)\eta,\qquad\text{VIII}$$

where $K_\omega$ is a proportionality constant that depends on the angular frequency, $\omega$, of the stirring bar, the temperature of the reaction mixture, and the geometries of the reaction vessel and the stirring blade. $K_\omega$ can be obtained through calibration with solutions of known viscosity.

During a polymerization, the viscosity of the reaction mixture increases over time due to the increase in molecular weight of the reaction product or polymer concentration or both. This change in viscosity can be monitored by measuring the applied torque and using equation VIII to convert the measured data to viscosity. In many instances, actual values for the viscosity are unnecessary, and one can dispense with the conversion step. For example, in situ measurements of applied torque can be used to rank reaction products based on molecular weight or conversion, as long as stirring rate, temperature, vessel geometry and stirring blade geometry are about the same for each reaction mixture.

Figure 23:
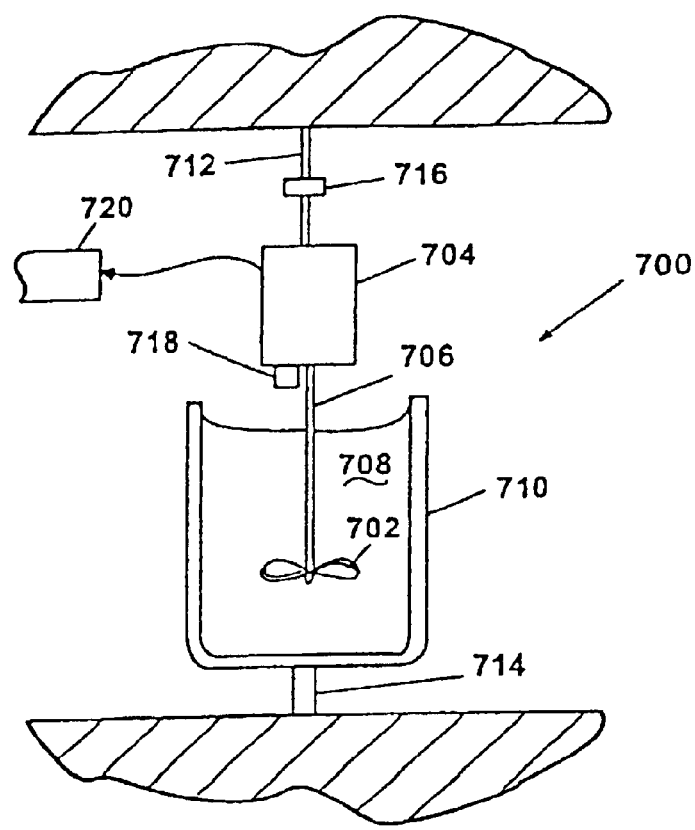
FIG. 23 illustrates an apparatus for directly measuring the applied torque of a stirring system.

FIG. 23 illustrates an apparatus 700 for directly measuring the applied torque. The apparatus 700 comprises a stirring blade 702 coupled to a drive motor 704 via a rigid drive spindle 706. The stirring blade 702 is immersed in a reaction mixture 708 contained within a reactor vessel 710. Upper 712 and lower 714 supports prevent the drive motor 704 and vessel 710 from rotating during operation of the stirring blade 702. For simplicity, the lower support 714 can be a permanent magnet. A torque or strain gauge 716 shown mounted between the upper support 712 and the drive motor 704 measures the average torque exerted by the motor 704 on the stirring blade 702. In alternate embodiments, the strain gauge 716 is inserted within the drive spindle 706 or is placed between the vessel 710 and the lower support 714. If located within the drive spindle 706, a system of brushes or commutators (not shown) are provided to allow communication with the rotating strain gauge. Often, placement of the strain gauge 716 between the vessel 710 and the lower support 714 is the best option since many stirring systems, such as the one shown in FIG. 10, use a single motor to drive multiple stirring blades.

Figure 24:
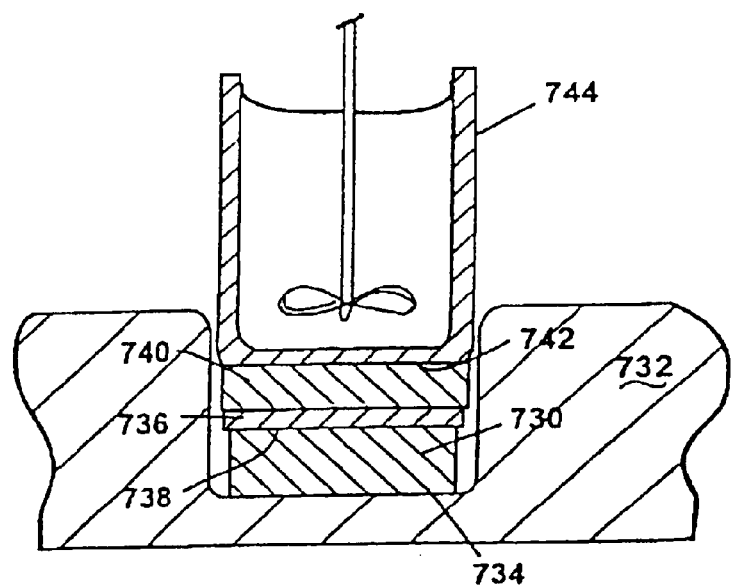
FIG. 24 shows placement of a strain gauge in a portion of a base plate that is similar to the lower plate of the reactor module shown in FIG. 10.

FIG. 24 shows placement of a strain gauge 730 in a portion of a base plate 732 that is similar to the lower plate 400 of the reactor module 390 shown in FIG. 10. The lower end 734 of the strain gauge 730 is rigidly attached to the base plate 732. A first permanent magnet 736 is mounted on the top end 738 of the strain gauge 730, and a second permanent magnet 740 is attached to the bottom 742 of a reactor vessel 744. When the vessel 744 is inserted in the base plate 732, the magnetic coupling between the first magnet 736 and the second magnet 740 prevents the vessel 744 from rotating and transmits torque to the strain gauge 730.

Besides using a strain gauge, one can also monitor drive motor power consumption, which is related to the applied torque. Referring again to FIG. 23, the method requires monitoring and control of the stirring blade 702 rotational speed, which can be accomplished by mounting a sensor 718 adjacent to the drive spindle 706. Suitable sensors 718 include optical detectors, which register the passage of a spot on the drive spindle 706 by a reflectance measurement, or which note the interruption of a light beam by an obstruction mounted on the drive spindle 706, or which discern the passage of a light beam through a slot on the drive spindle 706 or on a co-rotating obstruction. Other suitable sensors 718 include magnetic field detectors that sense the rotation of a permanent magnet affixed to the spindle 706. Operational details of magnetic field sensors are described below in the discussion of phase lag detection. Sensors such as encoders, resolvers, Hall effect sensors, and the like, are commonly integrated into the motor 704. An external processor 720 adjusts the power supplied to the drive motor 704 to maintain a constant spindle 706 rotational speed. By calibrating the required power against a series of liquids of known viscosity, the viscosity of an unknown reaction mixture can be determined.

In addition to direct measurement, torque can be determined indirectly by measuring the phase angle or phase lag between the stirring blade and the driving force or torque. Indirect measurement requires that the coupling between the driving torque and the stirring blade is "soft," so that significant and measurable phase lag occurs.

With magnetic stirring, "soft" coupling occurs automatically. The torque on the stirring bar is related to the magnetic moment of the stirring bar, $\mu$, and the amplitude of the magnetic field that drives the rotation of the stirring bar, H, through the expression $$\Gamma = \mu H \sin\theta,\qquad\text{IX}$$

where $\theta$ is the angle between the axis of the stirring bar (magnetic moment) and the direction of the magnetic field. At a given angular frequency, and for known $\mu$ and H, the phase angle, $\theta$, will automatically adjust itself to the value necessary to provide the amount of torque needed at that frequency. If the torque required to stir at frequency $\omega$ is proportional to the solution viscosity and the stirring frequency—an approximation useful for discussion—then the viscosity can be calculated from measurements of the phase angle using the equation $$\Gamma = \mu H \sin\theta = \alpha\eta\omega\qquad\text{X}$$

where $\alpha$ is a proportionality constant that depends on temperature, and the geometry of the vessel and the stirring blade. In practice, one may use equation VIII or a similar empirical expression for the right hand side of equation X if the torque does not depend linearly on the viscosity-frequency product.

Figure 25:
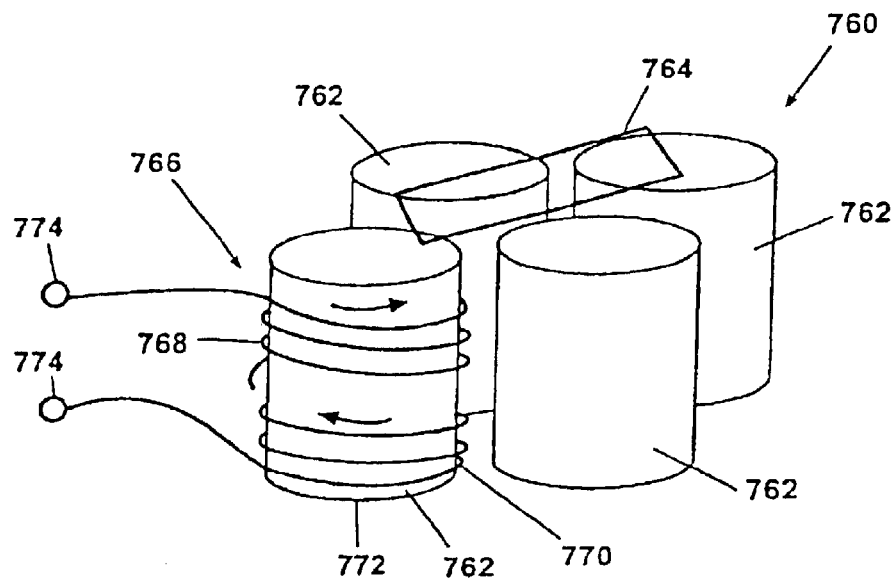
FIG. 25 shows an inductive sensing coil system for detecting rotation and measuring phase angle of a magnetic stirring blade or bar.

FIG. 25 shows an inductive sensing coil system 760 for measuring phase angle or phase lag, $\theta$. The system 760 comprises four electromagnets 762, which drive the magnetic stirring bar 764, and a phase-sensitive detector, such as a standard lock-in amplifier (not shown). A gradient coil 766 configuration is used to sense motion of the stirring bar 764, though many other well known inductive sensing coil configurations can be used. The gradient coil 766 is comprised of a first sensing coil 768 and a second sensing coil 770 that are connected in series and are wrapped in opposite directions around a first electromagnet 772. Because of their opposite polarities, any difference in voltages induced in the two sensing coils 768, 770 will appear as a voltage difference across the terminals 774, which is detected by the lock-in amplifier. If no stirring bar 764 is present, then the alternating magnetic field of the first electromagnet 772 will induce approximately equal voltages in each of the two coils 768, 770—assuming they are mounted symmetrically with respect to the first electromagnet 772—and the net voltage across the terminals 774 will be about zero. When a magnetic stirring bar 764 is present, the motion of the rotating magnet 764 will induce a voltage in each of the two sensing coils 768, 770. But, the voltage induced in the first coil 768, which is closer to the stirring bar 764, will be much larger than the voltage induced in the second coil 770, so that the voltage across the terminals 774 will be nonzero. A periodic signal will thus be induced in the sensing coils 768, 770, which is measured by the lock-in amplifier.

Figure 26:
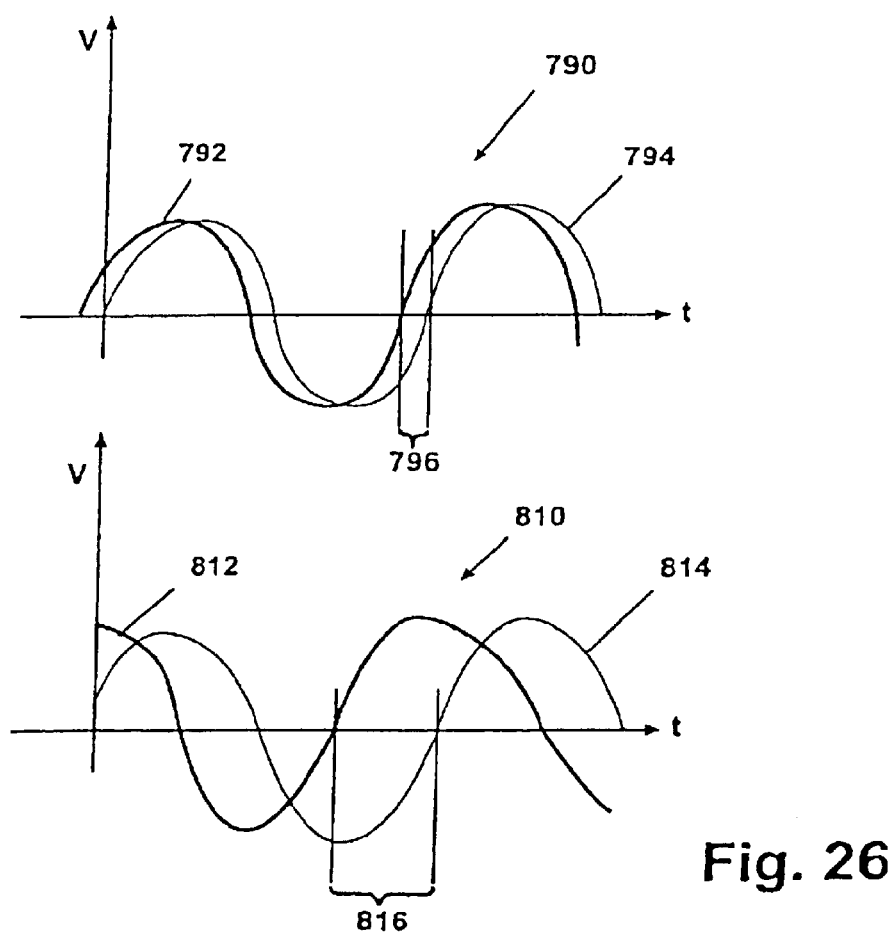
FIG. 26 shows typical outputs from inductive sensing coils, which illustrate phase lag associated with magnetic stirring for low and high viscosity solutions, respectively.
Figure 27:
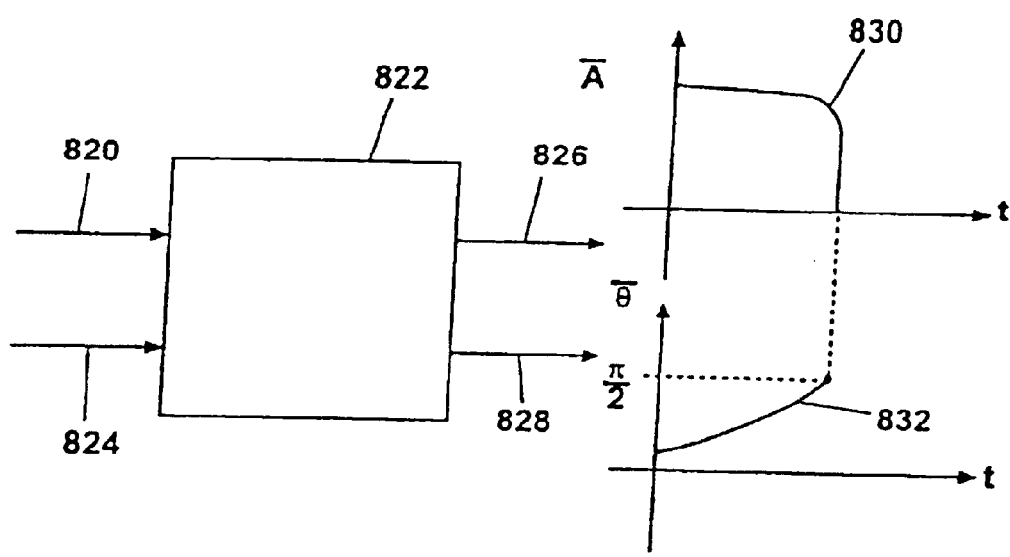
FIG. 27 illustrates how amplitude and phase angle will vary during a reaction as the viscosity increases from a low value to a value sufficient to stall the stirring bar.

FIG. 26 and FIG. 27 show typical outputs 790, 810 from the inductive sensing coil system 760 of FIG. 25, which illustrate phase lag associated with magnetic stirring for low and high viscosity solutions, respectively. Periodic signals 792, 812 from the sensing coils 768, 770 are plotted with sinusoidal reference signals 794, 814 used to drive the electromagnets. Time delay, At 796, 816, between the periodic signals 792, 812 and the reference signals 794, 814 is related to the phase angle by $\theta = \omega \cdot \Delta t$. Visually comparing the two outputs 790, 810 indicates that the phase angle associated with the high viscosity solution is larger than the phase angle associated with the low viscosity solution.

FIG. 27 illustrates how amplitude and phase angle will vary during a reaction as the viscosity increases from a low value to a value sufficient to stall the stirring bar. A waveform or signal 820 from the sensing coils is input to a lock-in amplifier 822, using the drive circuit sinusoidal current as a phase and frequency reference signal 824. The lock-in amplifier 822 outputs the amplitude 826 of the sensing coil signal 820, and phase angle 828 or phase lag relative to the reference signal 824. The maximum phase angle is $$\frac{\pi}{2}$$

radians, since, as shown by equation X, torque decreases with further increases in $\theta$ leading to slip of the stirring bar 764 of FIG. 25. Thus, as viscosity increases during reaction, the phase angle 828 or phase lag also increases until the stirring bar stalls, and the amplitude 826 abruptly drops to zero. This can be seen graphically in FIG. 27, which shows plots of $\overline{A}$ 830 and $\overline{\theta}$ 832, the amplitude of the reference signal and phase angle, respectively, averaged over many stirring bar rotations. One can optimize the sensitivity of the phase angle 828 measurement by proper choice of the magnetic field amplitude and frequency.

To minimize interference from neighboring stirring bars—ideally, each set of gradient coils should sense the motion of a single stirring bar—each vessel should be provided with electromagnets that are not shared with adjacent vessels. For example, a 4:1 magnet array shown in FIG. 14 should be used instead of the 2:1 or the 1:1 magnet arrays shown in FIGS. 13 and 12. In order to take readings from all of the vessels in an array, a multiplexer can be used to sequentially route signals from each vessel to the lock-in amplifier. Normally, an accurate measurement of the phase angle can be obtained after several tens of rotations of the stirring bars. For rotation frequencies of 10–20 Hz, this time will be on the order of a few seconds per vessel. Thus, phase angle measurements for an entire array of vessels can be typically made once every few minutes, depending on the number of vessels, the stirring bar frequency, and the desired accuracy. In order to speed up the measurement process, one may employ multiple-channel signal detection to measure the phase angle of stirring bars in more than one vessel at a time. Alternate detection methods include direct digitization of the coil output waveforms using a high-speed multiplexer and/or an analog-to-digital converter, followed by analysis of stored waveforms to determine amplitude and phase angle.

Phase angle measurements can also be made with non-magnetic, mechanical stirring drives, using the inductive coil system 760 of FIG. 25. For example, one may achieve sufficient phase lag between the stirring blade and the drive motor by joining them with a torsionally soft, flexible connector. Alternatively, the drive mechanism may use a resilient belt drive rather than a rigid gear drive to produce measurable phase lag. The stirring blade must include a permanent magnet oriented such that its magnetic moment is not parallel to the axis of rotation. For maximum sensitivity, the magnetic moment of the stirring blade should lie in the plane of rotation. Note that one advantage to using a non-magnetic stirring drive is that there is no upper limit on the phase angle.

In addition to directly or indirectly measuring torque, one may sense viscosity by increasing the driving frequency, $\omega_D$, or decreasing the magnetic field strength until, in either case, the stirring bar stalls because of insufficient torque. The point at which the stirring bar stops rotating can be detected using the same setup depicted in FIG. 25 for measuring phase angle. During a ramp up (down) of the driving frequency (field strength), the magnitude of the lock-in amplifier output will abruptly fall by a large amount when the stirring bar stalls. The frequency or field strength at which the stirring bar stalls can be correlated with viscosity: the lower the frequency or the higher the field strength at which stalling occurs, the greater the viscosity of the reaction mixture.

With appropriate calibration, the method can yield absolute viscosity data, but generally the method is used to rank reactions. For example, when screening multiple reaction mixtures, one may subject all of the vessels to a series of step changes in either frequency or field strength, while noting which stirring bars stall after each of the step changes. The order in which the stirring bars stall indicates the relative viscosity of the reaction mixtures since stirring bars immersed in mixtures having higher viscosity will stall early. Note that, in addition to providing data on torque and stall frequency, the inductive sensing coil system 760 of FIG. 25 and similar devices can be used as diagnostic tools to indicate whether a magnetic stirring bar has stopped rotating during a reaction.

Mechanical Oscillators

Piezoelectric quartz resonators or mechanical oscillators can be used to evaluate the viscosity of reaction mixtures, as well as a host of other material properties, including molecular weight, specific gravity, elasticity, dielectric constant, and conductivity. In a typical application, the mechanical oscillator, which can be as small as a few mm in length, is immersed in the reaction mixture. The response of the oscillator to an excitation signal is obtained for a range of input signal frequencies, and depends on the composition and properties of the reaction mixture. By calibrating the resonator with a set of well characterized liquid standards, the properties of the reaction mixture can be determined from the response of the mechanical oscillator. Further details on the use of piezoelectric quartz oscillators to measure material properties are described in co-pending U.S. patent application Ser. No. 09/133,171 "Method and Apparatus for Characterizing Materials by Using a Mechanical Resonator," filed Aug. 12, 1998, which is herein incorporated by reference.

Although many different kinds of mechanical oscillators currently exist, some are less useful for measuring properties of liquid solutions. For example, ultrasonic transducers or oscillators cannot be used in all liquids due to diffraction effects and steady acoustic (compressive) waves generated within the reactor vessel. These effects usually occur when the size of the oscillator and the vessel are not much greater than the characteristic wavelength of the acoustic waves. Thus, for reactor vessel diameters on the order of a few centimeters, the frequency of the mechanical oscillator should be above 1 MHz. Unfortunately, complex liquids and mixtures, including polymer solutions, often behave like elastic gels at these high frequencies, which results in inaccurate resonator response.

Often, shear-mode transducers as well as various surface-wave transducers can be used to avoid some of the problems associated with typical ultrasonic transducers. Because of the manner in which they vibrate, shear mode transducers generate viscous shear waves instead of acoustic waves. Since viscous shear waves decay exponentially with distance from the sensor surface, such sensors tend to be insensitive to the geometry of the measurement volume, thus eliminating most diffraction and reflection problems. Unfortunately, the operating frequency of these sensors is also high, which, as mentioned above, restricts their use to simple fluids. Moreover, at high vibration frequencies, most of the interaction between the sensor and the fluid is confined to a thin layer of liquid near the sensor surface. Any modification of the sensor surface through adsorption of solution components will often result in dramatic changes in the resonator response.

Figure 28:
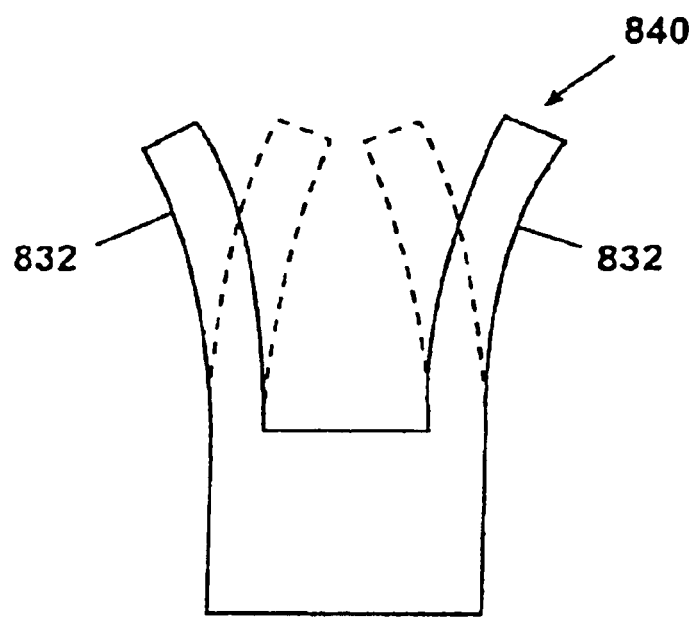
FIGS. 28–29 show bending modes of tuning forks and bimorph/unimorph resonators, respectively.
Figure 29:
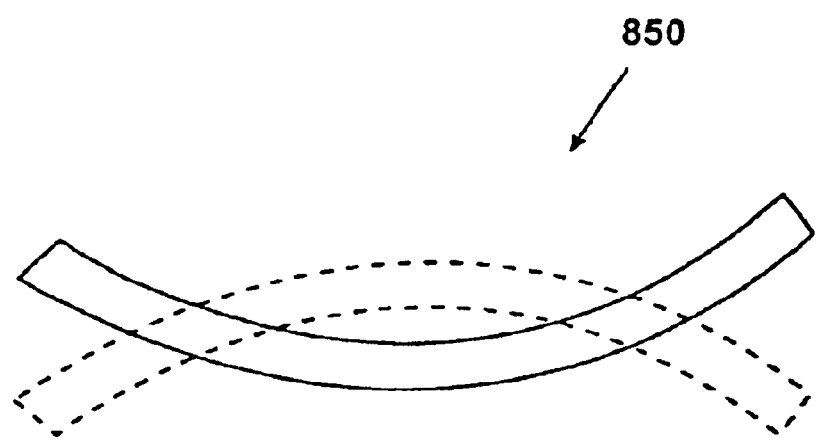

Tuning forks 840 and bimorph/unimorph resonators 850 shown in FIG. 28 and FIG. 29, respectively, overcome many of the drawbacks associated with ultrasonic transducers. Because of their small size, tuning forks 840 and bimorph/unimorph resonators 850 have difficulty exciting acoustic waves, which typically have wavelengths many times their size. Furthermore, though one might conclude otherwise based on the vibration mode shown in FIG. 28, tuning forks 840 generate virtually no acoustic waves: when excited, each of the tines 832 of the tuning fork 840 acts as a separate acoustic wave generator, but because the tines 832 oscillate in opposite directions and phases, the waves generated by each of the tines 832 cancel one another. Like the shear mode transducers described above, the bimorph/unimorph 850 resonators produce predominantly viscous waves and therefore tend to be insensitive to the geometry of the measurement volume. But unlike the shear mode transducers, bimorph/unimorph 850 resonators operate at much lower frequencies, and therefore can be used to measure properties of polymeric solutions.

Figure 30:
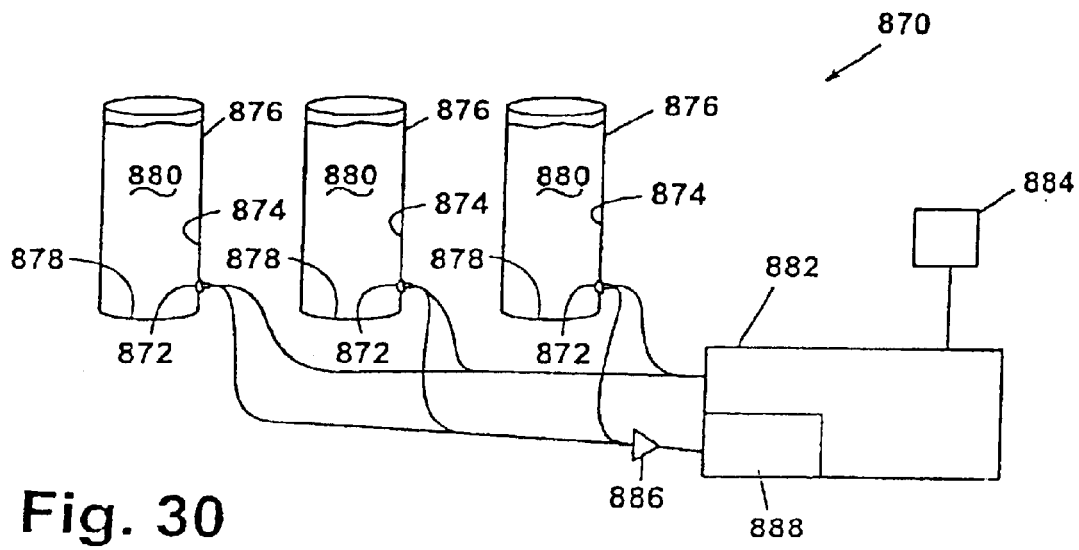
FIG. 30 schematically shows a system for measuring the properties of reaction mixtures using mechanical oscillators.

FIG. 30 schematically shows a system 870 for measuring the properties of reaction mixtures using mechanical oscillators 872. An important advantage of the system 870 is that it can be used to monitor the progress of a reaction. The oscillators 872 are mounted on the interior walls 874 of the reaction vessels 876. Alternatively, the oscillators 872 can be mounted along the bottom 878 of the vessels 876 or can be freestanding within the reaction mixtures 880. Each oscillator 872 communicates with a network analyzer 882 (for examples an HP8751A analyzer), which generates a variable frequency excitation signal. Each of the oscillators 872 also serve as receivers, transmitting their response signals back to the network analyzer 882 for processing. The network analyzer 882 records the responses of the oscillators 872 as functions of frequency, and sends the data to storage 884. The output signals of the oscillators 872 pass through a high impedance buffer amplifier 886 prior to measurement by the wide band receiver 888 of the network analyzer 882.

Other resonator designs may be used. For example, to improve the suppression of acoustic waves, a tuning fork resonator with four tines can be used. It is also possible to excite resonator oscillations through the use of voltage spikes instead of a frequency sweeping AC source. With voltage spike excitation, decaying free oscillations of the resonator are recorded instead of the frequency response. A variety of signal processing techniques well known to those of skill in the art can be used to distinguish resonator responses.

Alternate embodiments can be described with reference to the parallel reactor system 130 shown in FIG. 2. A single resonator (not shown) is attached to the 3-axis translation system 150. The translation system 150, at the direction of the processor 160, places the resonator within a reactor vessel of interest. A reading of resonator response is taken and compared to calibration curves, which relate the response to viscosity, molecular weight, specific gravity, or other properties. In another embodiment, a portion of the reaction mixture is withdrawn from a reactor vessel, using, for example, the liquid handling system 146, and is placed in a separate vessel containing a resonator. The response of the resonator is measured and compared to calibration data. Although the system 870 shown in FIG. 30 is better suited to monitor solution properties in situ, the two alternate embodiments can be used as post-characterization tools and are much simpler to implement.

In addition to mechanical oscillators, other types of sensors can be used to evaluate material properties. For example, interdigitated electrodes can be used to measure dielectric properties of the reaction mixtures.

Pressure Control System

Figure 31:
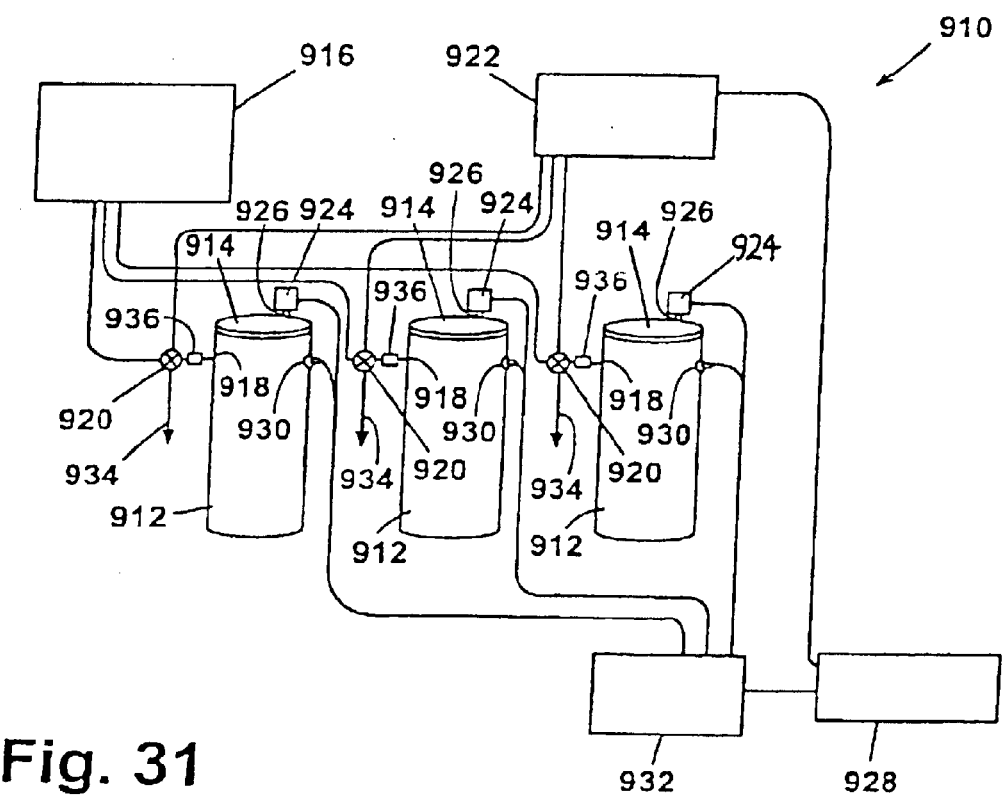
FIG. 31 shows an apparatus for assessing reaction kinetics based on monitoring pressure changes due to production or consumption various gases during reaction.

Another technique for assessing reaction kinetics is to monitor pressure changes due to production or consumption of various gases during reaction. One embodiment of this technique is shown in FIG. 31. A parallel reactor 910 comprises a group of reactor vessels 912. A gas-tight cap 914 seals each of the vessels 912 and prevents unintentional gas flow to or from the vessels 912. Prior to placement of the cap 914, each of the vessels 912 is loaded with liquid reactants, solvents, catalysts, and other condensed-phase reaction components using the liquid handling system 146 shown in FIG. 2. Gaseous reactants from source 916 are introduced into each of the vessels 912 through a gas inlet 918. Valves 920, which communicate with a controller 922, are used to fill the reaction vessels 912 with the requisite amount of gaseous reactants prior to reaction. A pressure sensor 924 communicates with the vessel head space—the volume within each of the vessels 912 that separates the cap 914 from the liquid components—through a port 926 located in the cap 914. The pressure sensors 924 are coupled to a processor 928, which manipulates and stores data. During reaction, any changes in the head space pressure, at constant temperature, reflect changes in the amount of gas present in the head space. This pressure data can be used to determine the molar production or consumption rate, $r_i$, of a gaseous component since, for an ideal gas at constant temperature, $$r_i = \frac{1}{RT}\frac{dp_i}{dt} \qquad \text{XI}$$

where R is the universal gas constant and $p_i$ is the partial pressure of the ith gaseous component. Temperature sensors 930, which communicate with the processor 928 through monitor 932, provide data that can be used to account for changes in pressure resulting from variations in head space temperature. The ideal gas law or similar equation of state can be used to calculate the pressure correction.

In an alternate embodiment, the valves 920 are used to compensate for the consumption of a gaseous reactant, in a reaction where there is a net loss in moles of gas-phase components. The valves 920 are regulated by the valve controller 922, which communicates with the processor 928. At the beginning of the reaction, the valves 920 open to allow gas from the high pressure source 916 to enter each of the vessels 912. Once the pressure within each of the vessels 912, as read by the sensor 924, reaches a predetermined value, $P_H$, the processor 928 closes the valves 920. As the reaction consumes the source 916 gas, the total pressure within each of the vessels 912 decreases. Once the pressure in a particular vessel 912 falls below a predetermined value, $P_L$, the processor 928 opens the valve 920 associated with the particular vessel 912, repressurizing it to $P_H$. This process—filling each of the vessels 912 with source 916 gas to $P_H$, allowing the head space pressure to drop below $P_L$, and then refilling the vessels 912 with source 916 gas to $P_H$—is usually repeated many times during the course of the reaction. Furthermore, the total pressure in the head space of each of the vessels 912 is continuously monitored and recorded during the gas fill-pressure decay cycle.

An analogous method can be used to investigate reactions where there is a net gain of gas-phase components. At the beginning of a reaction, all reaction materials are introduced into the vessels 912 and the valves 920 are closed. As the reaction proceeds, gas production results in a rise in head space pressure, which sensors 924 and processor 928 monitor and record. Once the pressure within a particular vessel 912 reaches $P_H$, the processor 928 directs the controller 922 to open the appropriate valve 920 to depressurize the vessel 912. The valve 920, which is a multi-port valve, vents the gas from the head space through an exhaust line 934. Once the head space pressure falls below $P_L$, the processor 928 instructs the controller 922 to close the valve 920. The total pressure is continuously monitored and recorded during the gas rise-vent cycle.

The gas consumption (production) rates can be estimated from the total pressure data by a variety of methods. For simplicity, these methods are described in terms of a single reactor vessel 912 and valve 920, but they apply equally well to a parallel reactor 910 comprising multiple vessels 912 and valves 920. One estimate of gas consumption (production) can be made from the slope of the pressure decay (growth) curves obtained when the valve is closed. These data, after converting total pressure to partial pressure based on reaction stoichiometry, can be inserted into equation XI to calculate $r_i$, the molar consumption (production) rate. A second estimate can be made by assuming that a fixed quantity of gas enters (exits) the vessel during each valve cycle. The frequency at which the reactor is repressurized (depressurized) is therefore proportional to the gas consumption (production) rate. A third, more accurate estimate can be obtained by assuming a known gas flow rate through the valve. Multiplying this value by the time during which the valve remains open yields an estimate for the quantity of gas that enters or leaves the vessel during a particular cycle. Dividing this product by the time between the next valve cycle—that is, the time it takes for the pressure in the vessel head space to fall from $P_H$ to $P_L$—yields an average value for the volumetric gas consumption (production) rate for the particular valve cycle. Summing the quantity of gas added during all of the cycles equals the total volume of gas consumed (produced) during the reaction.

The most accurate results are obtained by directly measuring the quantity of gas that flows through the valve. This can be done by noting the change in pressure that occurs during the time the valve is open—the ideal gas law can be used to convert this change to the volume of gas that enters or leaves the vessel. Dividing this quantity by the time between a particular valve cycle yields an average volumetric gas consumption (production) rate for that cycle. Summing the volume changes for each cycle yields the total volume of gas consumed (produced) in the reaction.

In an alternate embodiment shown in FIG. 31, the gas consumption rate is directly measured by inserting flow sensors 936 downstream of the valves 920 or by replacing the valves 920 with flow sensors 936. The flow sensors 936 allow continuous monitoring of the mass flow rate of gas entering each of the vessels 912 through the gas inlet 918. To ensure meaningful comparisons between experiments, the pressure of the source 916 gas should remain about constant during an experiment. Although the flow sensors 936 eliminate the need for cycling the valves 920, the minimum detectable flow rates of this embodiment are less than those employing pressure cycling. But, the use of flow sensors 936 is generally preferred for fast reactions where the reactant flow rates into the vessels 912 are greater than the threshold sensitivity of the flow sensors 936.

EXAMPLES

The following examples are intended as illustrative and non-limiting, and represent specific embodiments of the present invention.

Example 1

Calibration of Mechanical Oscillators For Measuring Molecular Weight

Mechanical oscillators were used to characterize reaction mixtures comprising polystyrene and toluene. To relate resonator response to the molecular weight of polystyrene, the system 870 illustrated in FIG. 30 was calibrated using polystyrene standards of known molecular weight dissolved in toluene. Each of the standard polystyrene-toluene solutions had the same concentration, and were run in separate (identical) vessels using tuning fork piezoelectric quartz resonators similar to the one shown in FIG. 28. Frequency response curves for each resonator were recorded at intervals between about 10 and 30 seconds.

Figure 32:
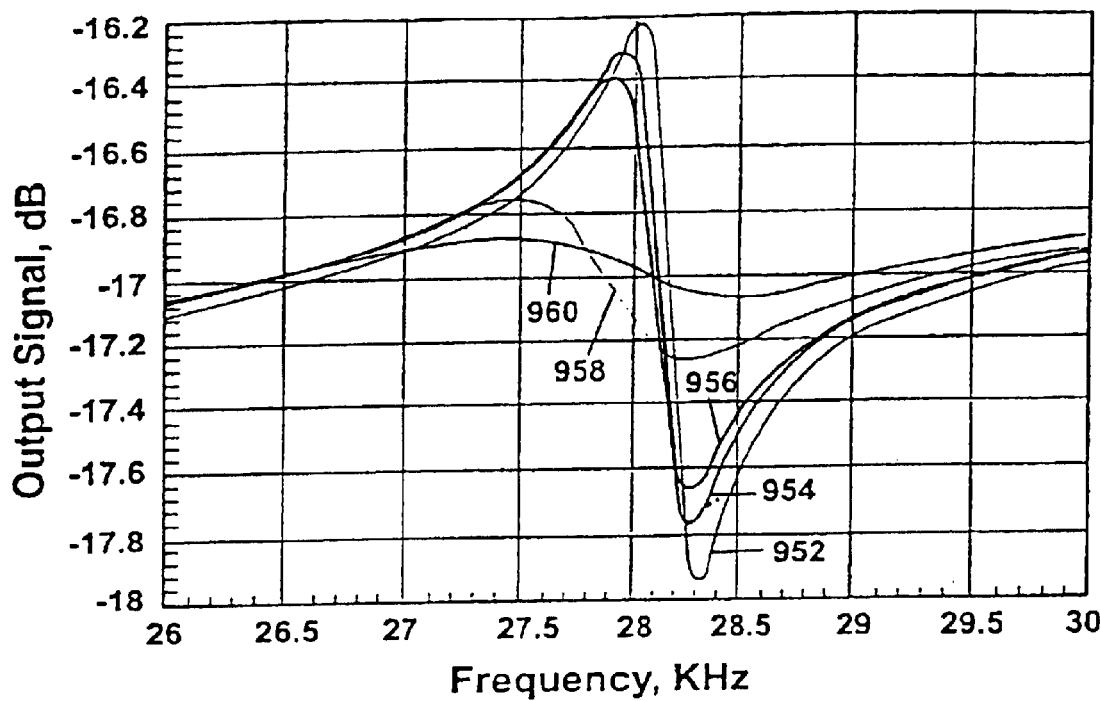
FIG. 32 shows results of calibration runs for polystyrene-toluene solutions using mechanical oscillators.

The calibration runs produced a set of resonator responses that could be used to relate the output from the oscillators 872 immersed in reaction mixtures to polystyrene molecular weight. FIG. 32 shows results of calibration runs 970 for the polystyrene-toluene solutions. The curves are plots of oscillator response for polystyrene-toluene solutions comprising no polystyrene 952, and polystyrene standards having weight average molecular weights ($M_w$) of $2.36 \times 10^3$ 954, $13.7 \times 10^3$ 956, $114.2 \times 10^3$ 958, and $1.88 \times 10^6$ 960.

Figure 33:
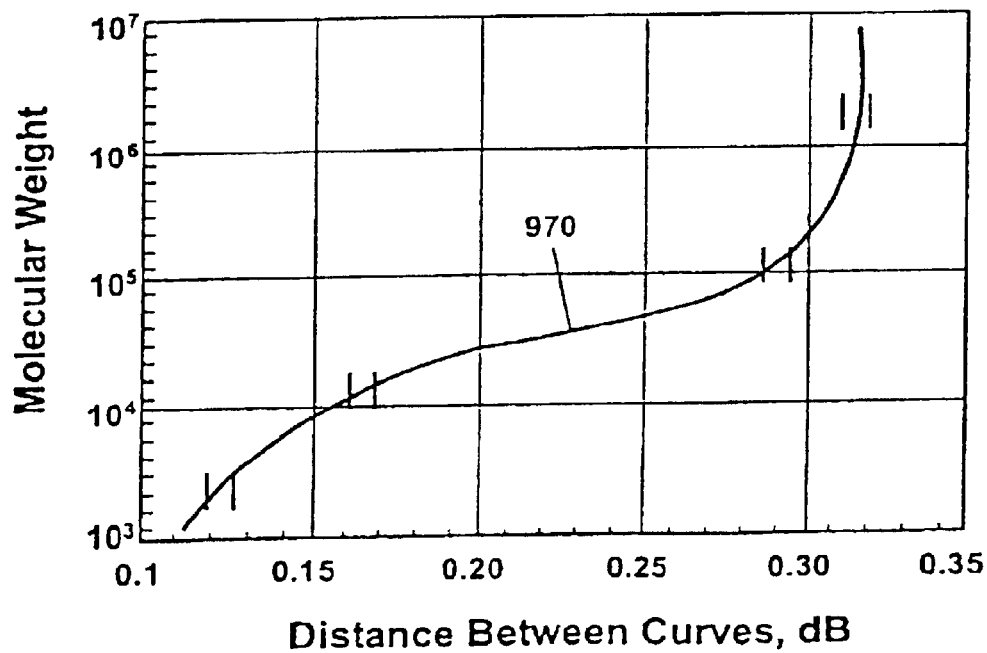
FIG. 33 shows a calibration curve obtained by correlating $M_w$ of the polystyrene standards with the distance between the frequency response curve for toluene and each of the polystyrene solutions of FIG. 32.

FIG. 33 shows a calibration curve 970 obtained by correlating $M_w$ of the polystyrene standards with the distance between the frequency response curve for toluene 952 and each of the polystyrene solutions 954, 956, 958, 960 of FIG. 32. This distance was calculated using the expression:

$$d_i = \sqrt{\frac{1}{f_1 - f_0} \int_{f_0}^{f_1} (R_0 - R_i)^2 \, df}, \qquad \text{XII}$$

where $f_0$ and $f_1$ are the lower and upper frequencies of the response curve, respectively; $R_0$ is the frequency response of the resonator in toluene, and $R_i$ is the resonator response in a particular polystyrene-toluene solution. Given response curves for an unknown polystyrene-toluene mixture and pure toluene 952 (FIG. 32), the distance between the two curves can be determined from equation XII. The resulting $d_i$ can be located along the calibration curve 970 of FIG. 33 to determine $M_w$ for the unknown polystyrene-toluene solution.

Example 2

Figure 34:
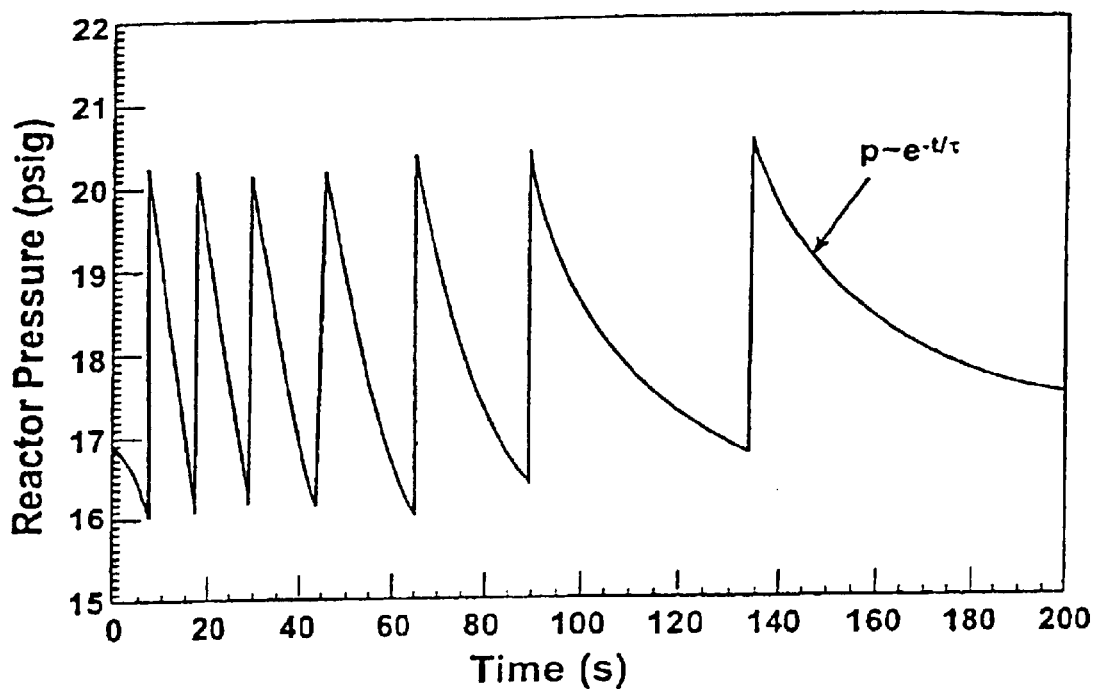
FIG. 34 depicts the pressure recorded during solution polymerization of ethylene to polyethylene.

Measurement of Gas-Phase Reactant Consumption by Pressure Monitoring and Control FIG. 34 depicts the pressure recorded during solution polymerization of ethylene to polyethylene. The reaction was carried out in an apparatus similar to that shown in FIG. 31. An ethylene gas source was used to compensate for ethylene consumed in the reaction. A valve, under control of a processor, admitted ethylene gas into the reaction vessel when the vessel head space pressure dropped below $P_L \approx 16.1$ psig due to consumption of ethylene. During the gas filling portion of the cycle, the valve remained open until the head space pressure exceeded $P_H \approx 20.3$ psig.

Figure 35:
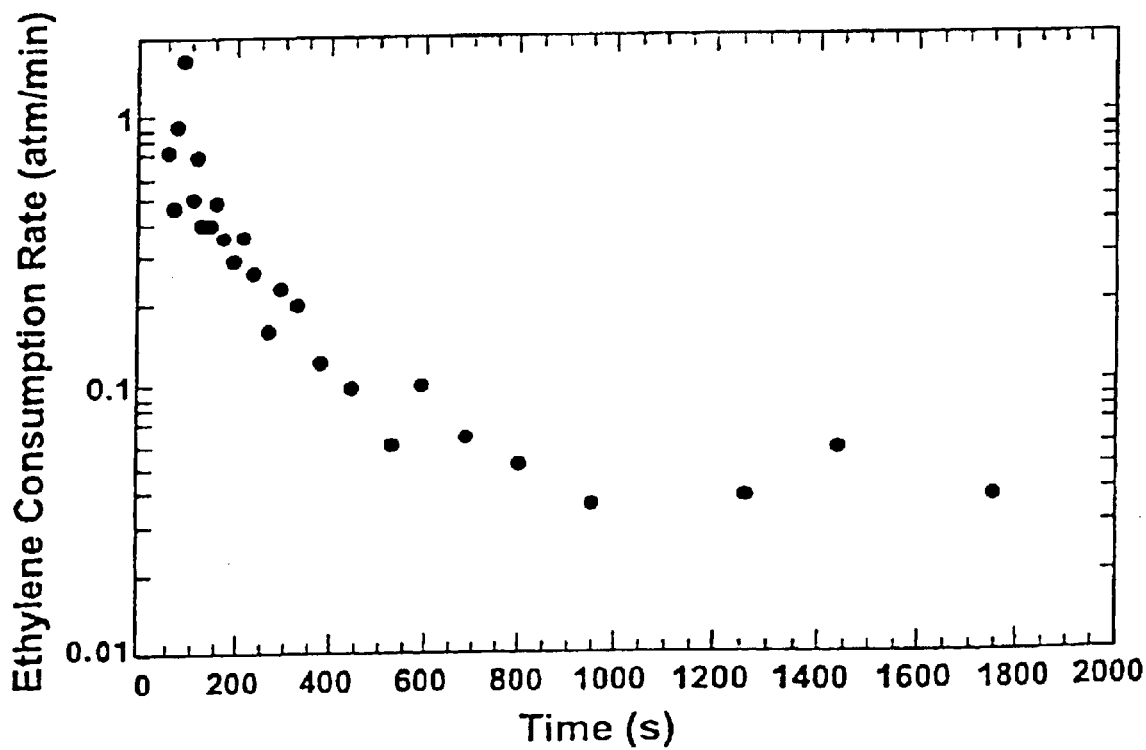
FIGS. 35–36 show ethylene consumption rate as a function of time, and the mass of polyethylene formed as a function of ethylene consumed, respectively.
Figure 36:
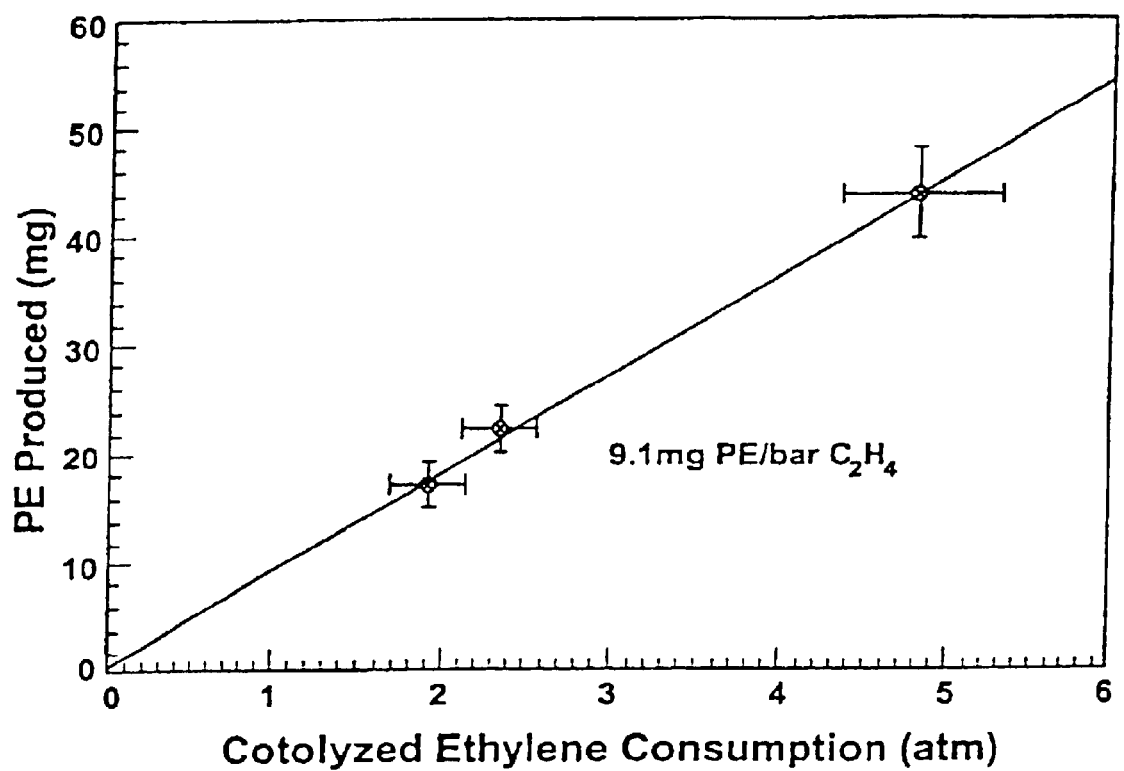

FIG. 35 and FIG. 36 show ethylene consumption rate as a function of time, and the mass of polyethylene formed as a function of ethylene consumed, respectively. The average ethylene consumption rate, $-r_{C2,k}(\text{atm} \cdot \text{min}^{-1})$, was determined from the expression $$-r_{C2,k} = \frac{(P_H - P_L)_k}{\Delta t_k} \qquad \text{XIII}$$

where subscript k refers to a particular valve cycle, and $\Delta t_k$ is the time interval between the valve closing during the present cycle and the valve opening at the beginning of the next cycle. As shown in FIG. 35, the constant ethylene consumption rate at later times results from catalyzed polymerization of ethylene. The high ethylene consumption rate early in the process results primarily from transport of ethylene into the catalyst solution prior to establishing an equilibrium ethylene concentration in the liquid phase. FIG. 36 shows the amount of polyethylene produced as a function of the amount of ethylene consumed by reaction. The amount of polyethylene produced was determined by weighing the reaction products, and the amount of ethylene consumed by reaction was estimated by multiplying the constant average consumption rate by the total reaction time. A linear least-squares fit to these data yields a slope which matches the value predicted from the ideal gas law and from knowledge of the reaction temperature and the total volume occupied by the gas (the product of vessel head space and number of valve cycles during the reaction).

Figure 37:
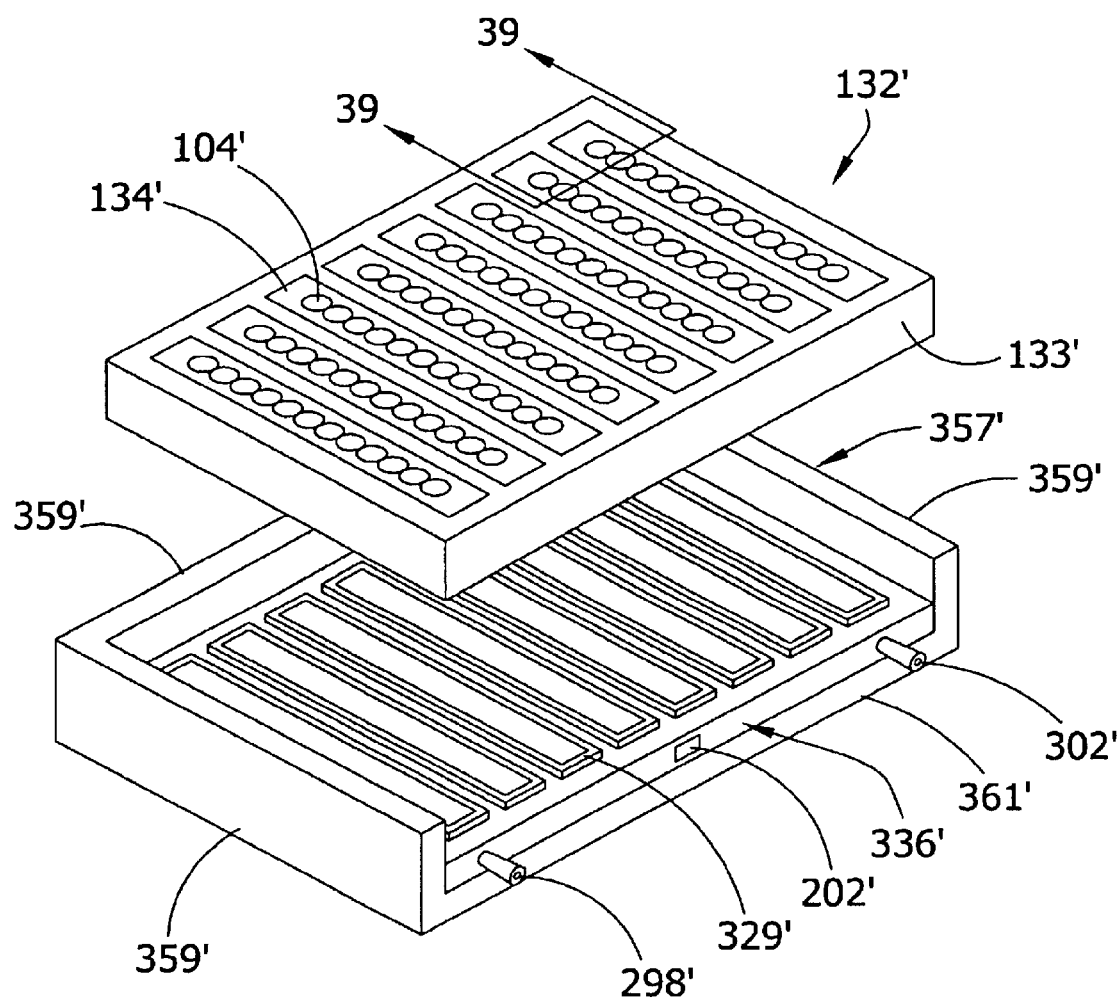
FIG. 37 is a schematic of an alternative embodiment of a multi-temperature modular reactor.
Figure 38:
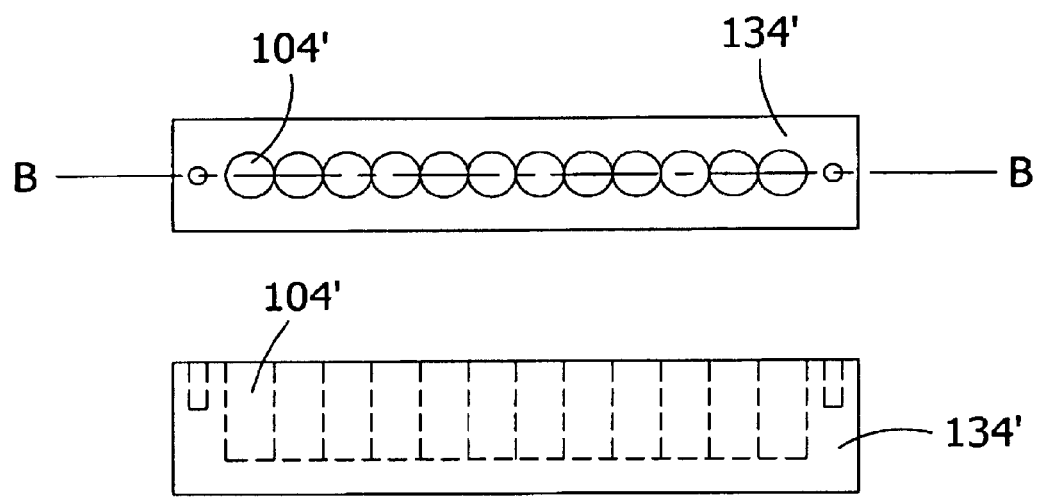
FIG. 38 is top and side view of a reactor block module.

Overview of a Multi-Temperature Modular Reactor For Use in a Parallel Reactor System FIG. 37 shows a perspective view of one embodiment of a multi-temperature modular reactor module 132' for use in a parallel reactor system 100. Modular reactor 132', similar to modular reactor 132 which has been previously described in reference to FIG. 2, includes a plurality of reactor modules 134' and a heat transfer plate 336'. Reactor modules 134', best seen in FIG. 38, each include a plurality of wells 104' for receiving removable reaction vessels (not shown) for containing therein an array of materials to be analyzed and characterized. While wells 104' may serve as reaction vessels, it is preferred that removable reaction vessels are used so that one can remove a subset of reaction vessels from reactor modules 134' for, e.g., further in-depth characterization. Further, reaction vessels, which are considerably lower in cost than reactor modules 134', may be discarded if damaged after use, without incurring great cost. In FIG. 38, wells 104' are shown as being aligned along a common axis B—B. However, it is understood that wells 104' may be arranged in any suitable manner along reactor module 134'. Further, while reactor module 134' is shown as having twelve wells 104' formed therein, any number of wells 104' may be provided.

Figure 39:
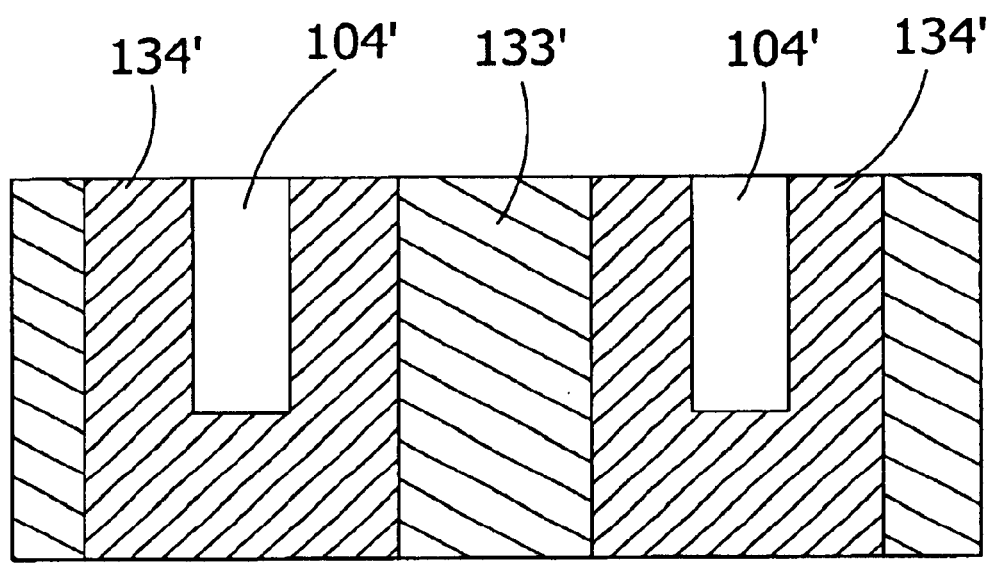
FIG. 39 is a cross-sectional view of two reactor modules in a storage rack taken along lines 39—39 in FIG. 37.

To properly position reactor modules 134' in modular reactor 132', there is provided a rack 133', as shown in FIGS. 37 and 39. Rack 133' includes a plurality of recesses 135' for selectively storing and properly positioning reactor modules 134' therein, where the number of recesses 135' corresponds to the number of reactor modules 134' that may be used with modular reactor 132'. Preferably, rack 133' is constructed of an insulating material, such as ceramic or other suitable materials, to insulate reactor modules 134' from one another, as best seen in FIG. 39. The function of the insulating material rack 133' will be explained more fully below.

Figure 40:
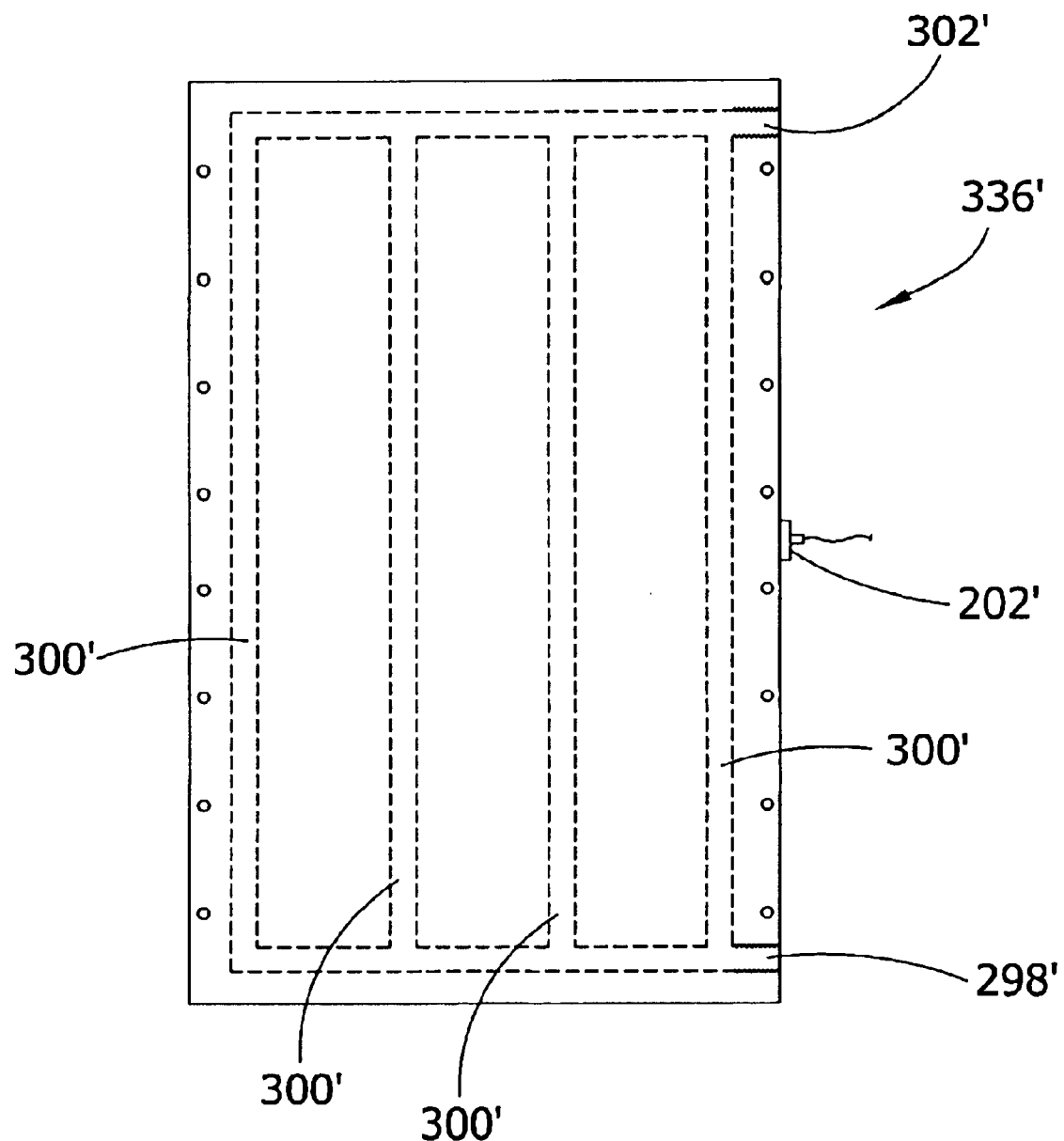
FIG. 40 is top view of a heat transfer plate.

Referring to FIGS. 37 and 40, heat transfer plate 336' is positioned below and in thermal contact with reactor modules 134' so as to subject reactor modules 134' to a first predetermined temperature. To accomplish this, heat transfer plate 336', which is constructed of a material having high thermal conductivity, such as aluminum, brass, etc., is provided with a plurality of passages 300' and inlet and outlet ports 298' and 302', respectively. A temperature control medium, such as a thermal fluid, is transported to heat transfer plate 336' using a pump (not shown) through inlet port 298'. Suitable thermal fluids include water, silicone oil and halogenated solvents (e.g., fluorinated, chlorinated, brominated), although other suitable fluids may also be employed. From inlet port 298', the thermal fluid flows through passages 300' formed in the heat transfer plate, eventually exiting heat transfer plate 336' at outlet port 302'. To improve the thermal contact between rack 133' and heat transfer plate 336', rack 133' may be positioned in mechanical contact with heat transfer plate 336' so as to permanently fixedly secured to heat transfer plate 336'. Mechanical contact may be achieved through the use of bolts, clips or other suitable fasteners.

In accordance with one aspect of the invention, it is preferred that heat transfer plate 336' is maintained substantially at a constant first predetermined temperature. This temperature may be above or below ambient temperature, depending upon the range of temperature values chosen for reactor modules 134', to be explained in greater detail below. To insure such a constant temperature, heat transfer plate 226' is provided with a temperature sensor 202' to monitor the temperature of heat transfer plate 336'. Suitable temperature sensors 202' include thermocouples, thermistors or resistance thermometric devices. Other sensors 202' may be employed as well.

Figure 41:
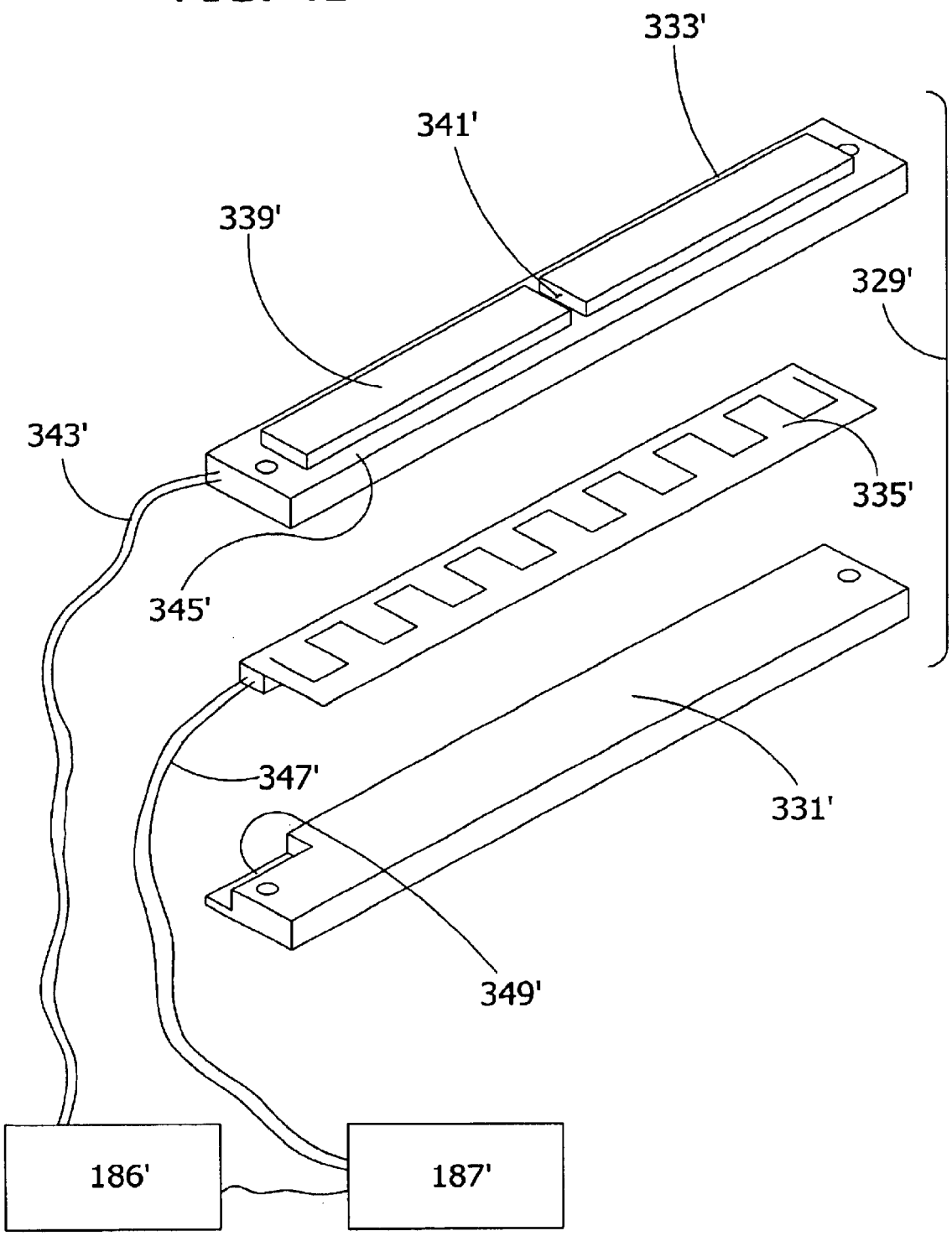
FIG. 41 is an exploded view of a temperature control unit for use with the multi-temperature modular reactor.

In accordance with one aspect of the present invention, referring to FIGS. 37 and 41, each reactor module 134' has associated with it a separate temperature control device 329', such that the number of reactor modules 134' is equal to the number of temperature control devices 329'. The temperature control devices 329' serve to independently vary the temperature of each reactor module 134' to a second predetermined temperature such that each reactor module 134' has a different second predetermined temperature. Further, the insulating material of the rack 133' that separates each reactor module 134' insures that heat is not transferred between each reactor module 134'.

In one embodiment, the temperature control device 329' is an electrical heating unit having a temperature control base plate 331', a temperature control top plate 333' and an electrical heating strip 335' with etched stainless steel circuit paths 337' encased in polyimide, such as those sold under the tradename Kapton™. The heating strip 335' is sandwiched between base plate 331' and top plate 333', with base plate 331' and top plate 333' being bolted together to form the electrical heating unit. The top plate 333' includes a raised center section 339' having a notch 341' therein for receiving a temperature sensor (not shown) similar to temperature sensor 202'. Leads 343' from temperature sensor 202' extend along a lower section 345' of top plate 333' to an external processor 186'. Wires 347' are connected to electrical heating strip 335' to permit power from electrical sources to vary the temperature of the electrical heating unit, and consequently the reactor modules 134'. To insure that wires 347' are not damaged when heating strip 335' is sandwiched between base plate 331' and top plate 333', base plate 331' preferably includes a recessed portion 349' through which wires 347' can safely extend.

In another embodiment the temperature control device 329' is a thermoelectric module. The thermoelectric module is constructed so as to be substantially identical to the electrical heating unit, except that a thermoelectric device replaces electrical heating strip 335'. The operation of temperature control devices 329' will be explained in greater detail below.

Referring back to FIG. 37, temperature control devices 329' may be fixedly secured to heat transfer plate 336', by bolting, bonding, welding or other suitable methods, such that temperature control devices 329' are positioned directly beneath reactor modules 134' and sandwiched between reactor modules 134' and heat transfer plate 336' when heat transfer plate 336' is in thermal contact with rack 133'. In an alternative embodiment, temperature control devices 329' may be permanently secured to each reactor module 134' or disposed directly within each reactor module 134', thereby resulting in an improved thermal contact between each temperature control device 329' and reactor module 134'.

Figure 42:
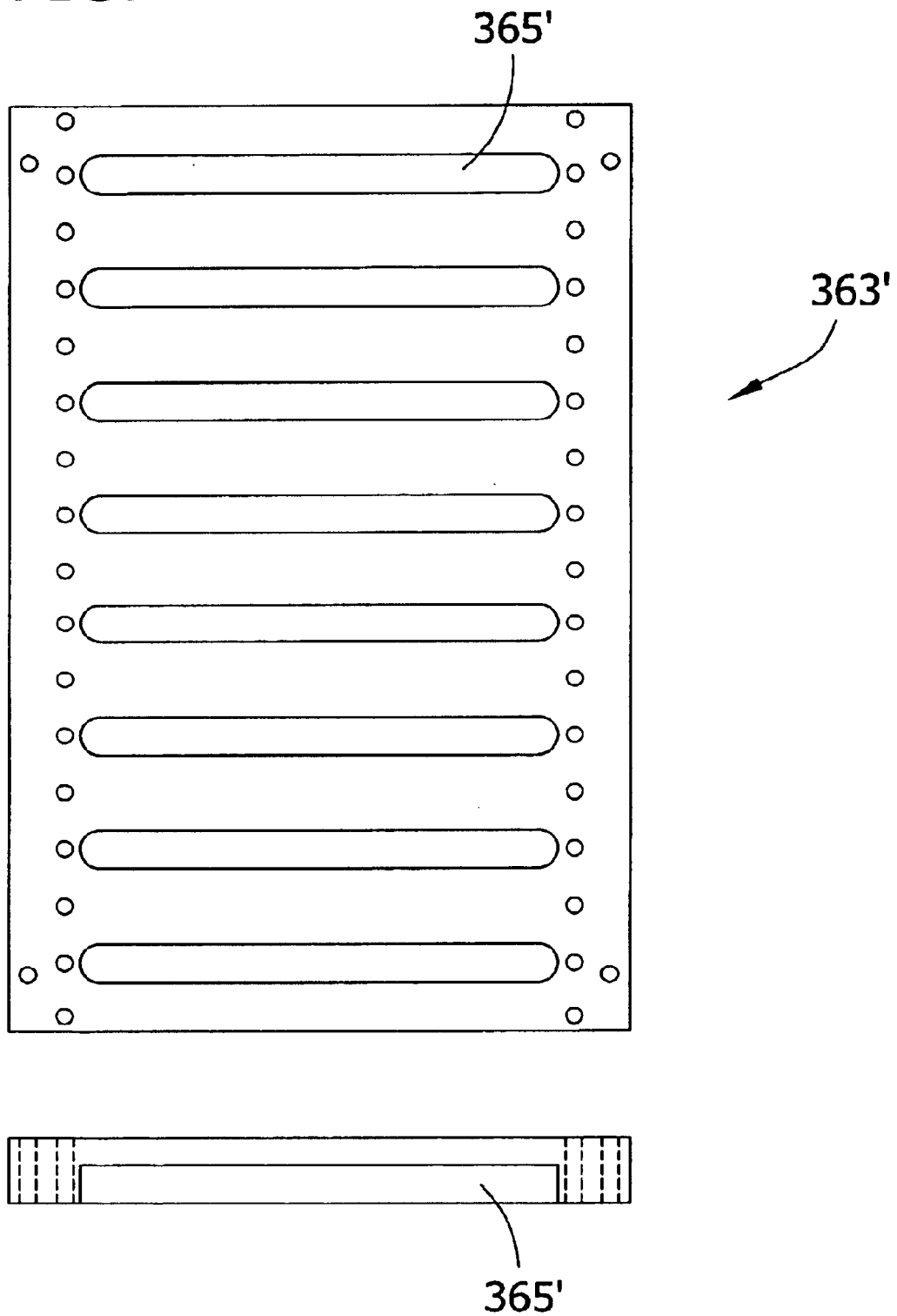
FIG. 42 is a planar view of the interior of a top plate for an insulating encasing.

Rack 133', storing reactor modules 134', temperature control devices 329' and heat transfer plate 336' are preferably arranged in an insulating casing 357', constructed of ceramic material, or other suitable insulating material, to thermally insulate modular reactor 132' from the environment. Casing 357' is constructed with sidewalls 359', a base plate 361' and a removable top plate 363' to permit access to the reaction vessels disposed in wells 104', as shown in FIG. 42. Top plate 363' includes a plurality of trough-like sections 365' that have a width that is greater than the diameter of wells 104' of reactor modules 134' and that are substantially aligned with wells 104'. Trough-like sections 365' are preferred to permit tops of the reaction vessels to extend into casing top plate 363' such that top plate 363' rests on upper surface 367' of rack 133', as opposed to the tops of the reaction vessels in wells 104', as walls of reaction vessels are relatively thin and may break under the weight of top plate 363'. Preferably, rack 133' is removable from casing 357' such that the entire array of materials may be removed from modular reactor 132' at one time.

Overview of the Operation of a Multi-Temperature Modular Reactor

To analyze, synthesize or characterize an array of materials, modular reactor 132' is assembled as described above in casing 357' with heat transfer plate 336' in thermal contact with rack 133'. Reaction vessels containing materials are then disposed in wells 104' in reactor modules 134' and top plate 363' of casing 357' is secured onto casing 357' to insulate modular reactor 132'. Heat transfer plate 336' is next brought to and substantially maintained at a constant first predetermined temperature that is below ambient temperature. The first predetermined temperature is achieved by constantly circulating thermal fluid through passages 300' in heat transfer plate 336' to bias rack 133', the reactor modules 134' and reaction vessels containing material therein to the first predetermined temperature.

Next, the temperature control devices 329' vary the temperature of each of the reactor modules 134' from the first predetermined temperature to a second predetermined temperature. Second predetermined temperature may be greater than or less than the first predetermined temperature of heat transfer plate 336' depending upon the characteristics of the materials under study. Preferably, each reactor module 134' has a different second predetermined temperature such that the characteristics of the materials in each reactor module 134' may be compared and contrasted with one another to determine the effect of temperature on reactions of the materials in the array.

The reactor modules 134' and heat transfer plate 336' are monitored by temperature sensors 202' which send signals to the processor 186'. The processor 186' simultaneously collects and analyzes temperature data received from all of the reactor modules 134' and heat transfer plate 336' and generates signals to a power supply 371'. The power supply 371', which is connected to temperature control device 329' by wires 347' produces a current in response to the temperature data received by processor 186' to vary the temperature of the temperature control device 329' which is transferred to the reactor modules 134'.

Electrical heating units, which convert electric power to heat, are desirable for use as the temperature control devices 329' in situations where it is desired to maintain all of reactor modules 134' at temperatures substantially greater than that of heat transfer plate 336'. Such units are available in a wide range of power levels, permitting the performance characteristics of the heating units to be matched to the requirements of the materials and reactions under study at a relatively low cost. In situations where one or more reactor modules 134' are to be maintained at temperatures below that of heat transfer plate 336', or in applications where rapid heating and cooling of reactor modules 336' is necessary, thermoelectric devices may be employed. Thermoelectric devices primarily serve as heat pumps, employing the Peltier effect to pump heat from one side of the device to the other when a direct electrical current is applied in a predetermined direction. When current is directed through the thermoelectric devices in a first predetermined direction, heat is pumped from heat transfer plate 336' to reactor blocks 134' to increase the temperature of reactor modules 134'. When the direction of electrical current is reversed to a second predetermined direction, heat is pumped from the reactor modules 134' to heat transfer plate 336', thereby reducing the temperature of the reactor modules 134'.

Once the temperature of the reactor modules 134' are varied, temperature sensors 202' cooperate with processor 186' to simultaneously evaluate the data collected and changes in the material in the reaction vessels are detected. The detecting and monitoring step may be performed at predefined intervals of time, such that characteristics of the array of materials may be performed as a function of time. Alternatively, the temperature of the reactor modules 134' may be varied at a predetermined rate such that the characteristics of the materials may be evaluated as a function of temperature.

In an alternative embodiment, the temperature may be independently varied over time for each reactor module 134'. One purpose is to vary the thermal history of samples in each module. Another purpose is to allow for different reaction times or different conditions in different reactor modules. For example, different modules may be maintained at the same temperature (e.g., the first predetermined temperature or second predetermined temperature) for different lengths of time. Another example is where different modules have different time/temperature profiles (such as heating or cooling different modules at different rates). A further example is where different modules are maintained at different temperatures for different time periods. Those of skill in the art will recognize different time/temperature profiles that can be accomplished with this system. This function can be controlled manually or automatically and may be accomplished by simply turning control on or off at specified times to one or more of the temperature control devices, discussed above. Thus, one or more of the reactor modules 134' may be allowed to come to ambient temperature or to the first or second predetermined temperature. The first predetermined temperature may be above or below ambient temperature. The temperature of each reactor module may be varied independently on the basis of another measured property or condition, such as viscosity, gas uptake, heat evolution, color change, dielectric constant, etc.

The above description is intended to be illustrative and not restrictive. Many embodiments as well as many applications besides the examples provided will be apparent to those of skill in the art upon reading the above description. The scope of the invention should therefore be determined, not with reference to the above description, but should instead be determined with reference to the appended claims, along with the full scope of equivalents to which such claims are entitled. The disclosures of all articles and references, including patent applications and publications, are incorporated by reference for all purposes.

What is claimed:

1. A modular reactor for analyzing chemical reactions in an array of materials, comprising
    at least two reactor modules, each of said reactor modules having at least one reactor vessel for receiving materials to be analyzed therein,
    a temperature control device associated with at least one of said reactor modules, wherein said temperature control device varies the temperature of said at least one reactor module such that said at least one reactor module has a different temperature than the other of said at least two reactor modules, and
    an analytical system comprising one or more sensors for in-situ evaluation of viscosity of the materials in each of the reactor vessels.

2. The reactor in claim 1, further including insulating material between said at least two reactor modules.

3. The reactor in claim 1, wherein said temperature control device is disposed within said reactor module.

4. The reactor in claim 1, wherein said temperature control device is an electrical heating strip.

5. The reactor in claim 4, wherein said electrical heating strip is selected from the group consisting of etched stainless steel circuit paths encased in silicon rubber, etched stainless steel circuit paths encased in polyimide, or resistive wire encased in a ceramic and metal sheath.

6. The reactor in claim 4, wherein said electrical heating strip is sandwiched between a heater base plate and a heater top plate to form an electrical heating unit, said electrical heating unit being positioned between at least one reactor module and a heat transfer plate that is in thermal contact with said at least two reactor modules.

7. The reactor in claim 6, wherein said heat transfer plate is in mechanical contact with said at least two reactor modules.

8. The reactor in claim 1, further including a temperature sensor in thermal contact with each of said at least two reactor modules for monitoring the temperature of said at least two reactor modules.

9. The reactor in claim 8, wherein said temperature sensor is one of a thermocouple, thermistor or resistance thermometric devices.

10. The reactor in claim 9, further including a processor connected to said temperature sensors for collecting and analyzing temperature data from each of said at least two reactor modules, wherein said processor produces a signal to vary the temperature of said at least two reactor modules.

11. The reactor of claim 1 wherein each of the reactor modules comprises a plurality of reactor vessels.

12. The reactor of claims 1 or 11 wherein the reactor vessels are wells.

13. The reactor of claims 1 or 11 wherein the reactor vessels are removable liners.

14. The reactor of claims 1 or 11 wherein the reactor vessels are pressure vessels or are individually contained in pressure vessels, and the reactor further comprises a pressure monitoring or control system associated with each of the reactor vessels.

15. The reactor of claim 1 further comprising a base plate, the at least two reactor modules being movably coupled to the base plate.

16. The reactor of claim 15 wherein the at least two reactor modules are movably coupled to the base plate for linear movement substantially within the plane of the base plate.

17. The reactor of claim 15 wherein the reactor modules are movably coupled to the base plate by reactor module guides adapted to mate with channels on the surface of the base plate.

18. The reactor of claim 1 further comprising a temperature control system comprising (i) a first temperature control device for commonly biasing said at least two reactor modules to a first predetermined temperature, said first temperature control device being in thermal contact with said at least two reactor modules, (ii) a second temperature control device associated with one of the at least two reactor modules for selectively varying the temperature of said at least one reactor module to a second predetermined temperature, and (iii) a third temperature control device associated with another of the at least two reactor modules for selectively varying the temperature of the another reactor module to a third predetermined temperature, said first predetermined temperature being different from each of said second and third predetermined temperatures.

19. The reactor of claim 1 further comprising a stirring blade in each of the reactor vessels, wherein the one or more sensors measure the effect of viscous forces on stirring blade rotation.

20. The reactor of claim 19 wherein the one or more sensors measure the applied torque required to maintain a constant angular velocity of the stirring blade.

21. The reactor of claim 19 wherein the one or more sensors include a strain gauge associated with each of the stirring blades.

22. The reactor of claim 19 wherein the one or more sensors measure the power consumption of a drive motor associated with the stirring blade.

23. The reactor of claim 19 wherein the one or more sensors include an optical detector associated with each of the stirring blades.

24. The reactor of claim 19 wherein the one or more sensors include a magnetic field detector associated with each of the stirring blades.

25. The reactor of claim 19 wherein the one or more sensors include an inductive coil sensor.

26. The reactor of claim 1 further wherein the one or more sensors include a resonator or mechanical oscillator.

27. The reactor of claim 26 wherein the one or more sensors include a shear-mode transducer.

28. The reactor of claim 26 wherein the one or more sensors include a tuning fork.

29. The reactor of claim 26 wherein the one or more sensors include a unimorph resonator.

30. The reactor of claim 26 wherein the one or more sensors include a bimorph resonator.

31. The reactor in claim 1, further including a heat transfer plate in thermal contact with said at least two reactor modules.

32. The reactor in claim 31, wherein said heat transfer plate further includes a plurality of passages for receiving a temperature control medium.

33. The reactor in claim 32, wherein said temperature control medium is a thermal fluid.

34. The reactor in claim 33, wherein said thermal fluid is a member of the set consisting of water, silicone oil and halogenated solvents.

35. The reactor in claim 31, wherein said temperature control device is fixedly secured to said at least one reactor module.

36. The reactor in claim 31, wherein said temperature control device is fixedly secured to said heat transfer plate.

37. The reactor in claim 31, wherein said temperature control device is a thermoelectric module.

38. The reactor in claim 37, wherein said thermoelectric module includes a heater base plate, a heater top plate and a thermoelectric device, said thermoelectric device being sandwiched between said heater base plate and said heater top plate.

39. The reactor in claim 37, wherein said thermoelectric module is sandwiched between said at least one reactor module and said heat transfer plate.

40. The reactor in claim 31, further including a rack for storing said at least two reactor modules.

41. The reactor in claim 40, wherein said heat transfer plate is fixedly secured to said rack.

42. The reactor in claim 40, further including an insulating casing for storing said rack and said heat transfer plate.

43. The reactor in claim 42, wherein said casing has a selectively removable top plate.

44. The reactor in claim 43, wherein said rack is selectively removable from said casing.

45. A method for analyzing, synthesizing or characterizing an array of materials comprising the steps of
providing a modular reactor comprising at least two reactor modules, each of the reactor modules having at least one reactor vessel,
placing material in said reactor vessels,
independently controlling the temperature of the at least two reactor modules to different predetermined temperatures, and
evaluating the viscosity of the materials in situ in each of the reactor vessels.

46. The method in claim 45, wherein evaluating the viscosity of the materials comprises monitoring and detecting changes in the materials at predefined intervals of time and determining viscosity of the materials as a function of time based on the detected changes.

47. The method in claim 46, further comprising varying the temperature of the reactor modules at a predetermined rate, wherein the viscosity of the materials is determined as a function of temperature.

48. The method in claim 46, wherein determining viscosity includes comparing the detected changes of said materials in said at least two reactor modules.

49. The method in claim 45, wherein said reactor modules are insulated from one another.

50. The method in claim 49, wherein said at least two reactor modules are insulated from environmental conditions.

51. The method of claim 45, wherein the modular reactor further comprises a heat transfer plate in thermal contact with said at least two reactor modules.

52. The method of claim 51 wherein controlling the temperature of the at least two reactor modules comprises biasing the at least two reactor modules using said heat transfer plate to a first predetermined temperature and independently varying the temperature of said at least two reactor modules using a separate temperature control device associated with each of the reactor modules.

53. The method of claim 52, wherein said first predetermined temperature is below ambient.

54. The method of claim 52, wherein said first predetermined temperature of said at least two reactor modules is maintained constant over time.

55. The method of claim 52, wherein said step of varying the temperature of said at least two reactor modules includes varying the temperature of each of said at least two reactor modules to a second and third predetermined temperature, respectively, wherein said second and third predetermined temperatures are different from each other and from said first predetermined temperature.

56. The method of claim 55, wherein said second and third predetermined temperatures are varied above said first predetermined temperature.

57. The method of claim 51 further comprising continuously flowing a thermal fluid through passages disposed in said heat transfer plate.

58. The method of claim 51, wherein said step of controlling the temperature of said reactor modules includes varying the amount of electric power supplied to separate temperature control devices associated with each of the at least two reactor modules.

59. The method of claim 45, wherein said temperature of said at least two reactor modules are controlled to vary over time.

60. The method of claim 45, wherein the viscosity of the materials are evaluated over time and said temperature of said at least two reactor modules is independently controlled based on the determined viscosity.

61. The method of claim 45 wherein the viscosity of the materials in each of the reactor vessels is evaluated in situ by stirring the materials in each of the reactor vessels using a stirring blade, and measuring the effect of viscous forces on stirring blade rotation.

62. The method of claim 61 wherein the viscosity is evaluated by measuring the applied torque required to maintain a constant angular velocity of the stirring blade.

63. The method of claim 61 wherein the viscosity is evaluated by measuring the power consumption of a drive motor associated with the stirring blade.

64. The method of claim 61 wherein the viscosity is evaluated by measuring the phase angle between the stirring blade and an associated driving force.

65. The method of claim 45 further wherein the viscosity of materials in each of the reactor vessels is evaluated in situ using a resonator or mechanical oscillator.

66. The method of claim 65 wherein a variable frequency excitation signal is applied to the resonator or mechanical oscillator.

67. The method of claim 65 wherein the resonator or mechanical oscillator is a tuning fork.

68. The method of claim 45 further comprising commonly biasing the at least two reactor modules to a predetermined temperature.

69. The method of claim 45 wherein each of the reactor modules comprises a plurality of reactor vessels.

70. The method of claims 45 or 69 wherein the reactor vessels are wells.

71. The method of claims 45 or 69 wherein the reactor vessels are removable liners.

72. The method of claims 45 or 69 farther comprising pressuring each of the reactor vessels and monitoring or controlling the pressure of each of the reactor vessels.

* * * * *

UNITED STATES PATENT AND TRADEMARK OFFICE
CERTIFICATE OF CORRECTION

PATENT NO. : 6,818,183 B2
DATED : November 16, 2004
INVENTOR(S) : Damian A. Hajduk et al.

It is certified that error appears in the above-identified patent and that said Letters Patent is hereby corrected as shown below:

Column 34,
Line 63, "farther" should read -- further --.

Signed and Sealed this

Twenty-fourth Day of May, 2005

JON W. DUDAS
*Director of the United States Patent and Trademark Office*